United States Patent
Hone et al.

(10) Patent No.: US 11,053,201 B2
(45) Date of Patent: Jul. 6, 2021

(54) CRYSTALLINE FORMS

(71) Applicant: SYNGENTA PARTICIPATIONS AG, Basel (CH)

(72) Inventors: John Hone, Bracknell (GB); Ian Kevin Jones, Bracknell (GB)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 16/969,798

(22) PCT Filed: Feb. 11, 2019

(86) PCT No.: PCT/EP2019/053292
§ 371 (c)(1),
(2) Date: Aug. 13, 2020

(87) PCT Pub. No.: WO2019/158476
PCT Pub. Date: Aug. 22, 2019

(65) Prior Publication Data
US 2020/0369614 A1    Nov. 26, 2020

(30) Foreign Application Priority Data
Feb. 13, 2018 (EP) .................................. 18156463

(51) Int. Cl.
  C07D 213/82 (2006.01)
  A01N 43/40 (2006.01)
(52) U.S. Cl.
  CPC .......... *C07D 213/82* (2013.01); *A01N 43/40* (2013.01); *C07B 2200/13* (2013.01)
(58) Field of Classification Search
  None
  See application file for complete search history.

(56) References Cited

U.S. PATENT DOCUMENTS 9,414,589 B2 *   8/2016   O'Sullivan ............ A01N 37/18
9,867,371 B2 *   1/2018   O'Sullivan ........... C07C 233/23

FOREIGN PATENT DOCUMENTS

WO      2015003951 A1    1/2015

OTHER PUBLICATIONS

International Search Report and Written Opinion for International Application No. PCT/EP2019/053292 dated Mar. 28, 2019.
European Extended Search Report dated Jun. 12, 2018 for EP Application No. 18156463.4.
Caira Ed, et al: "Crystalline Polymorphism of Organic Compounds"; Topics in Current Chemistry; Springer, Berlin, DE; vol. 198, pp. 163-208, 1998 (XP008166276).

* cited by examiner

*Primary Examiner* — Brian J Davis
(74) *Attorney, Agent, or Firm* — Baker & Hostetler LLP; Toni-Junell Herbert

(57) ABSTRACT

The invention relates to crystalline forms of N-[2-(2,4-dichlorophenyl)cyclobutyl]-2-(trifluoromethyl)pyridine-3-carboxamide of formula (I), compositions comprising said crystalline forms and methods of their use as nematicides or fungicides.

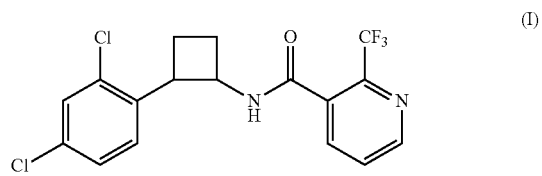

14 Claims, 14 Drawing Sheets

Figure 1:
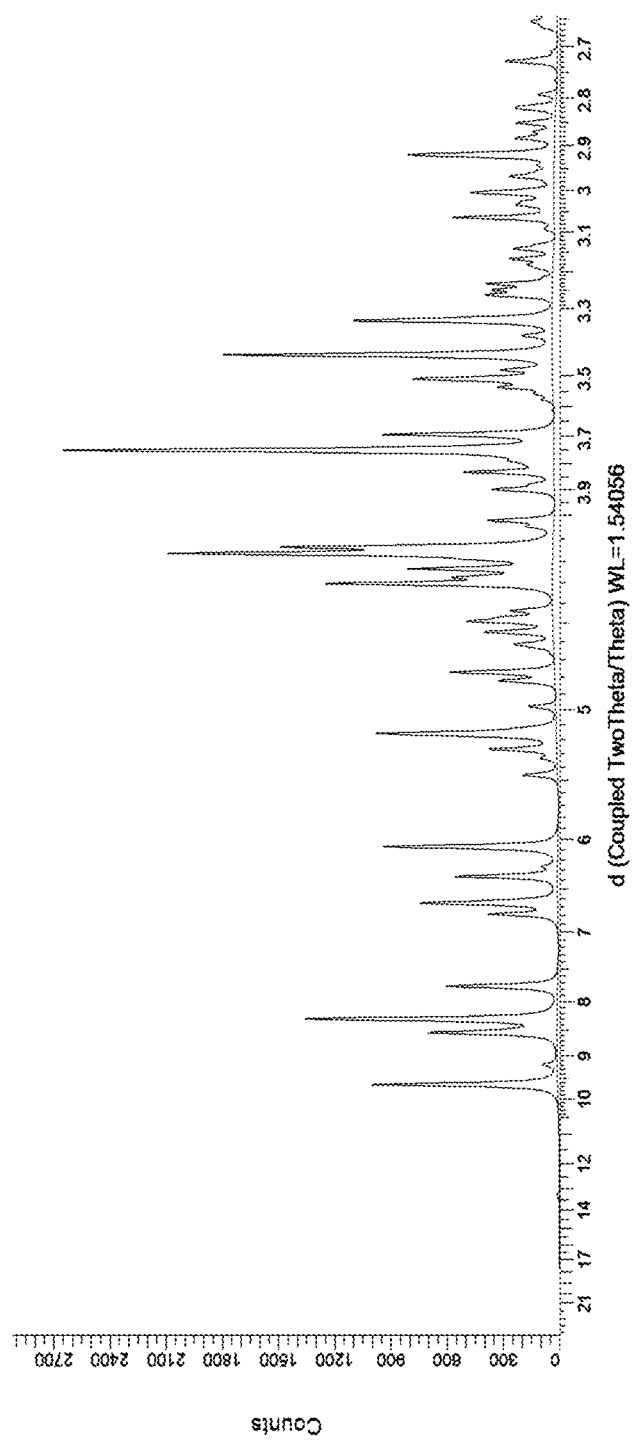

Figures 13a, 13b and 13c:
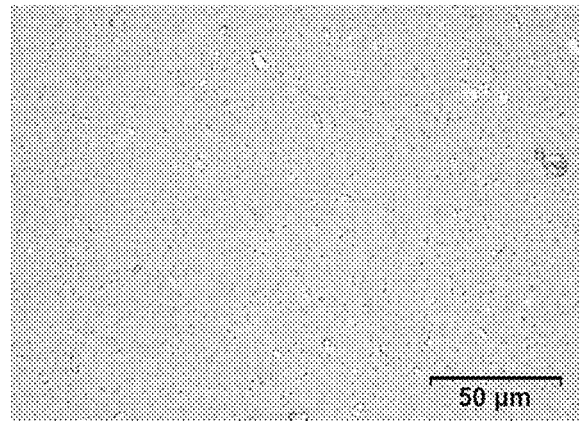
Figure 13a
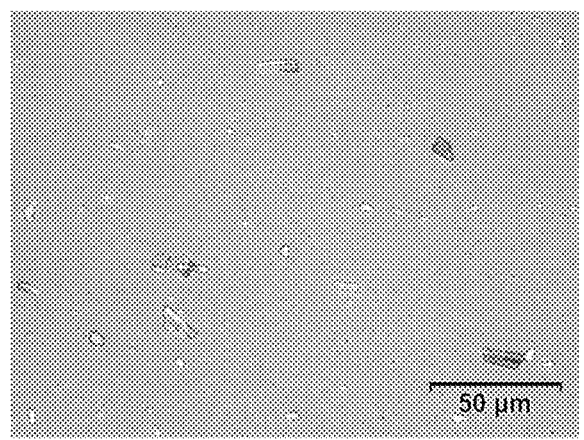
Figure 13b
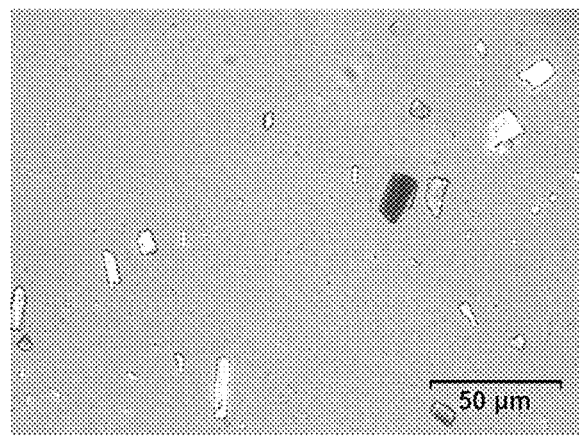
Figure 13c

Figures 14a, 14b and 14c:
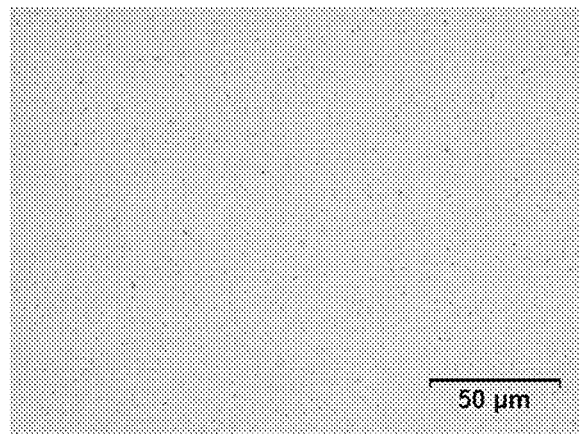
Figure 14a
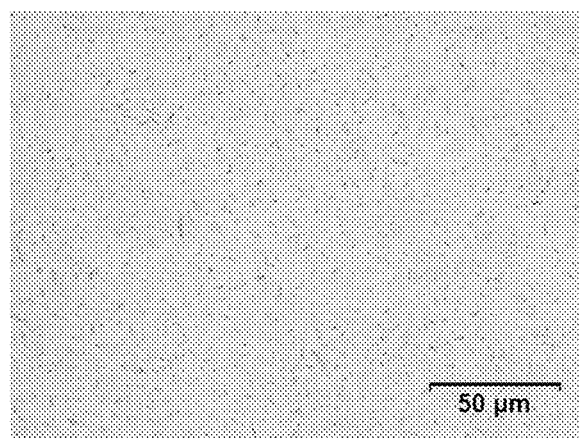
Figure 14b
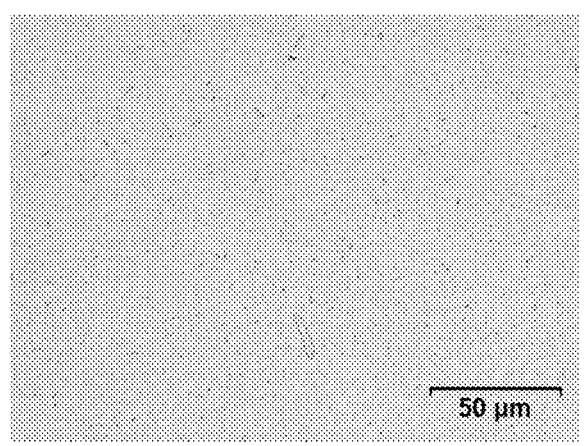
Figure 14c

CRYSTALLINE FORMS

CROSS-REFERENCE TO RELATED APPLICATIONS

This application is a 371 National Stage application of International Application No. PCT/EP2019/053292 filed Feb. 11, 2019 which claims priority to EP 18156463.4, filed Feb. 13, 2018, the entire contents of which applications are hereby incorporated by reference.

TECHNICAL FIELD

The invention relates to crystalline forms of N-[2-(2,4-dichlorophenyl)cyclobutyl]-2-(trifluoromethyl)pyridine-3-carboxamide, compositions comprising said crystalline forms and methods of their use as nematicides or fungicides.

BACKGROUND

WO2013/143811 discloses methods for preparing the compound cis-N-[2-(2,4-dichlorophenyl)cyclobutyl]-2-(trifluoromethyl)pyridine-3-carboxamide which is a racemate of the two enantiomers N-[(1S,2S)-2-(2,4-dichlorophenyl)cyclobutyl]-2-(trifluoromethyl)pyridine-3-carboxamide and N-[(1R,2R)-2-(2,4-dichlorophenyl)cyclobutyl]-2-(trifluoromethyl)pyridine-3-carboxamide. Cis-N-[2-(2,4-dichlorophenyl)cyclobutyl]-2-(trifluoromethyl)pyridine-3-carboxamide is exemplified in Table 57, example 57.011

WO2015/003951 discloses methods for preparing the enantiomer N-[(1S,2S)-2-(2,4-dichlorophenyl)cyclobutyl]-2-(trifluoromethyl)pyridine-3-carboxamide (Example P5). This compound is disclosed as a nematicide active against a wide range of nematodes.

Agrochemical compositions comprising cis-N-[2-(2,4-dichlorophenyl)cyclobutyl]-2-(trifluoromethyl)pyridine-3-carboxamide or its enantiomer N-[(1S,2S)-2-(2,4-dichlorophenyl)cyclobutyl]-2-(trifluoromethyl)pyridine-3-carboxamide have generically been disclosed in both WO2013/143811 and WO2015/003951. However, the application of certain types of formulations is dependent on the particular form, i.e. polymorphic or amorphous form, used to prepare the formulation. For example, if the form used to prepare a suspension concentrate (SC) is not stable in such a SC formulation, polymorphic conversion might occur in the formulation leading to unwanted crystal growth. Such crystal growth may be detrimental because it may lead to thickening and potentially solidification of the formulation which can in turn lead to blockages in application equipment, e.g. in spray nozzles in agricultural application machinery. Hence, there is a need to provide stable crystalline forms of the above compound to prepare agricultural or pharmaceutical formulations thereof.

DETAILED DESCRIPTION

In the context of the present invention, a polymorph is a particular crystal form of a chemical compound that can exist in more than one crystal form in the solid state. A crystal form of a compound contains the constituent molecules arranged in orderly repeating patterns extending in all three spatial dimensions (in contrast, an amorphous solid form has no long-range order in the position of molecules). Different polymorphs of a compound have different arrangements of atoms and or molecules in their crystal structure. When the compound is a biologically active compound, such as a nematicide, the difference in crystal structures can lead to different polymorphs having differing chemical, physical and biological properties. Properties which may be affected include crystal shape, density, hardness, colour, chemical stability, melting peak, hydroscopicity, suspensibility, dissolution rate and biological availability. As such, a specific polymorph may have properties which make it more advantageous in a particular use relative to another polymorph of the same compound: in particular, the physical, chemical and biological properties listed above can have a significant effect on the development of production methods and formulations, the ease with which a compound can be combined in a formulation with other active ingredients and formulation components and the quality and efficacy of plant treatment agents, such as nematicides. It is noted that predicting whether the solid state of a compound may be present as more than one polymorph is not possible and it is also not possible to predict the properties of any of these crystal forms.

Four polymorphic forms (Form A, B, C and D) of N-[2-(2,4-dichlorophenyl)cyclobutyl]-2-(trifluoromethyl)pyridine-3-carboxamide are disclosed herein. Methods for preparing Form A have been disclosed in WO2015/003951 (Example P5). Methods for preparing Form D have been disclosed in WO2013/143811 (Table 57, example 57.011).

Several techniques are commonly used to characterize polymorphs. For example, powder X-ray diffraction (pXRD) techniques are often used, other techniques which may be used include differential scanning calorimetry (DSC), thermogravimetric analysis (TGA) and Raman or Infra-red spectroscopy, nuclear magnetic resonance (NMR), gas chromatography, HPLC and in particular single crystal X-ray diffraction.

Hence, in a first aspect, the present invention provides a crystalline form (Form B) of N-[2-(2,4-dichlorophenyl)cyclobutyl]-2-(trifluoromethyl)pyridine-3-carboxamide of formula (I)

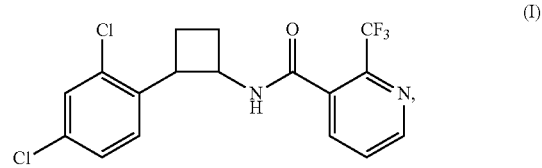 [SMILES: O=C(NC1CCC1c1ccc(Cl)cc1Cl)c1cccnc1C(F)(F)F]

characterized by an X-ray powder diffraction pattern comprising four or more 2-theta angle values selected from the group of 6.1±0.2, 11.2±0.2, 14.0±0.2, 16.7±0.2, 17.2±0.2, 18.5±0.2, 20.8±0.2, 21.3±0.2, 22.3±0.2, 23.6±0.2, 23.9±0.2 and 24.5±0.2 at a temperature of 21-26° C.

In one embodiment of the first aspect, the crystalline form (Form B) is characterized by a powder X-ray diffraction pattern comprising six or more 2-theta angle values selected from the group of 6.1±0.2, 11.2±0.2, 14.0±0.2, 16.7±0.2, 17.2±0.2, 18.5±0.2, 20.8±0.2, 21.3±0.2, 22.3±0.2, 23.6±0.2, 23.9±0.2 and 24.5±0.2 at a temperature of 21-26° C.

In one embodiment of the first aspect, the crystalline form (Form B) is characterized by a powder X-ray diffraction pattern comprising the 2-theta angle values selected from the group of 6.1±0.2, 11.2±0.2, 14.0±0.2, 16.7±0.2, 17.2±0.2, 18.5±0.2, 20.8±0.2, 21.3±0.2, 22.3±0.2, 23.6±0.2, 23.9±0.2 and 24.5±0.2 at a temperature of 21-26° C.

Figure 5:
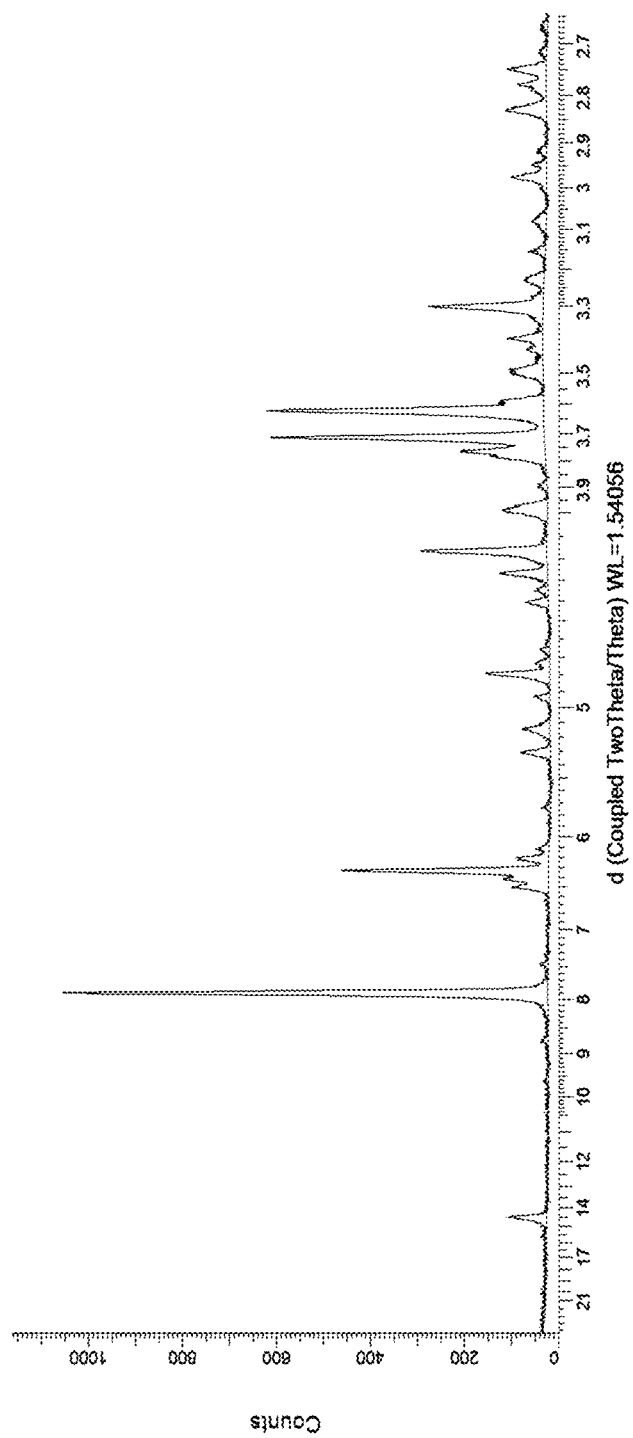

In another embodiment of the first aspect, the crystalline form (Form B) has an X-ray powder diffraction pattern which is substantially the same as the X-ray powder diffraction spectrum shown in FIG. 5 at a temperature of 21-26° C.

In another embodiment of the first aspect, the crystalline form (Form B) is further characterized by the following unit cell parameters:

a=15.52 Å±0.01 Å, b=7.24 Å±0.01 Å, c=16.64 Å±0.01 Å, α=90°±0.01°, ß=105.03±0.01°, γ=90°±0.01°, Z=4.

Form B represents a monohydrate polymorph of the enantiomer (1S,2S) N-[2-(2,4-dichlorophenyl)cyclobutyl]-2-(trifluoromethyl)pyridine-3-carboxamide.

Figure 6:
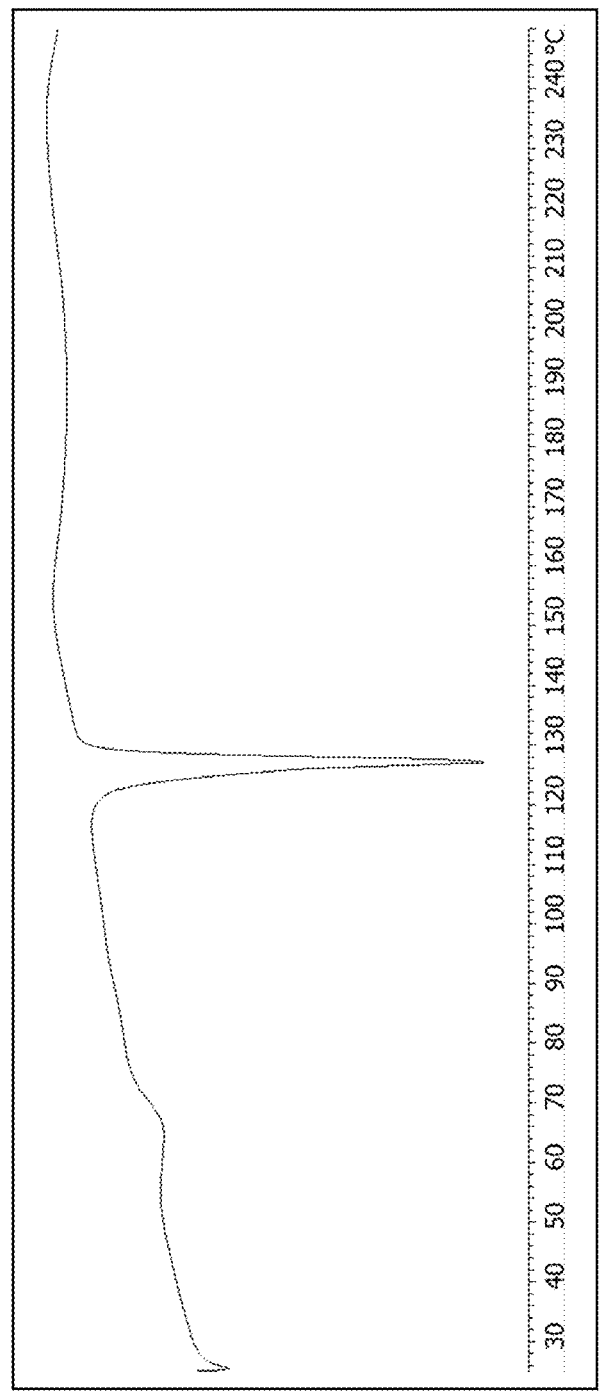

In yet another embodiment of the first aspect, the melting peak of the crystalline form (Form B) is a broad water endotherm in the DSC trace at about 65° C. (FIG. 6).

In a second aspect, the present invention describes a crystalline form (Form C) of N-[2-(2,4-dichlorophenyl)cyclobutyl]-2-(trifluoromethyl)pyridine-3-carboxamide of formula (I)

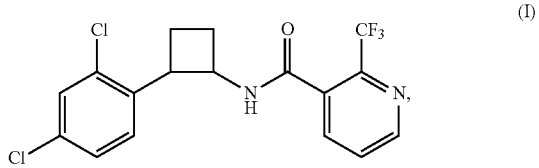 [SMILES: O=C(NC1CCC1c1ccc(Cl)cc1Cl)c1cccnc1C(F)(F)F]

(I)

characterized by an powder X-ray diffraction pattern comprising four or more 2-theta angle values selected from the group of 10.8±0.2, 14.5±0.2, 17.5±0.2, 19.0±0.2, 23.5±0.2, 24.5±0.2, 26.0±0.2, 30.2±0.2, 32.6±0.2, 33.3±0.2, 34.1±0.2 and 35.5±0.2 at a temperature of 21-26° C.

In one embodiment of the second aspect, the crystalline form (Form C) is characterized by an X-10.8±0.2, 14.5±0.2, 17.5±0.2, 19.0±0.2, 23.5±0.2, 24.5±0.2, 26.0±0.2, 30.2±0.2, 32.6±0.2, 33.3±0.2, 34.1±0.2 and 35.5±0.2 at a temperature of 21-26° C.

In one embodiment of the second aspect, the crystalline form (Form C) is characterized by an X-ray powder diffraction pattern comprising the 2-theta angle values selected from the group of 10.8±0.2, 14.5±0.2, 17.5±0.2, 19.0±0.2, 23.5±0.2, 24.5±0.2, 26.0±0.2, 30.2±0.2, 32.6±0.2, 33.3±0.2, 34.1±0.2 and 35.5±0.2 at a temperature of 21-26° C.

Figure 8:
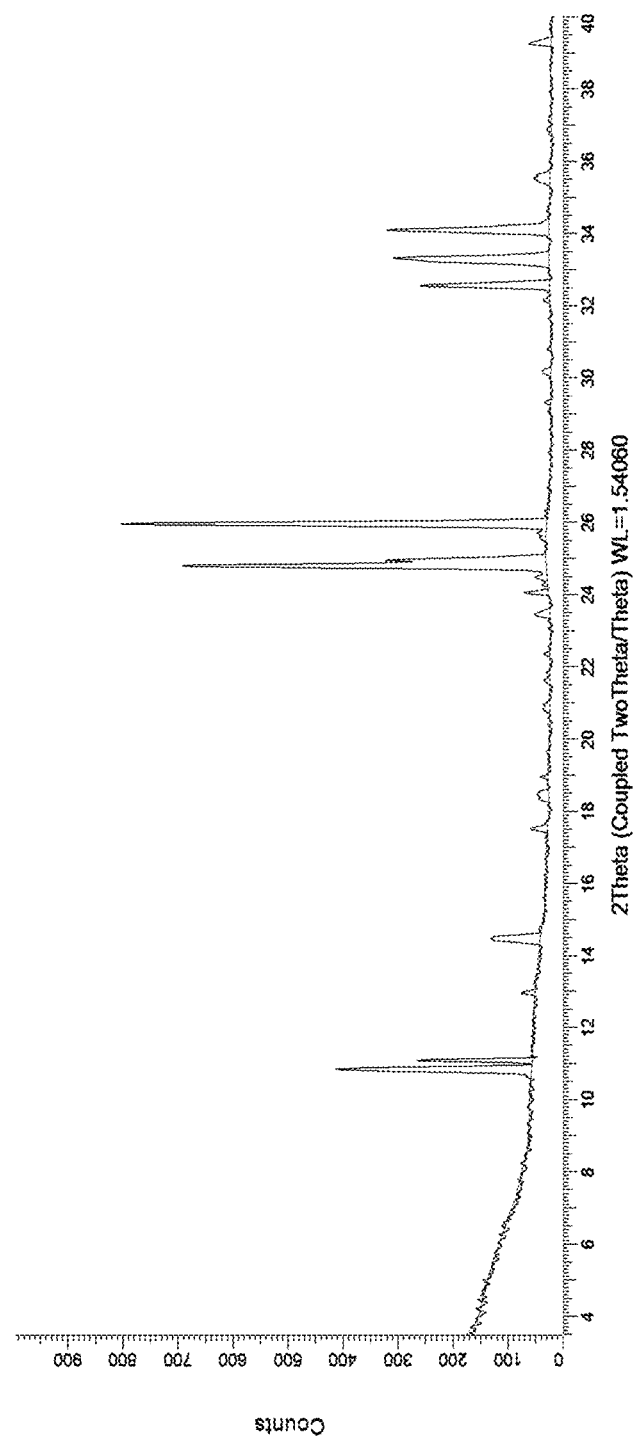
Figure 9:
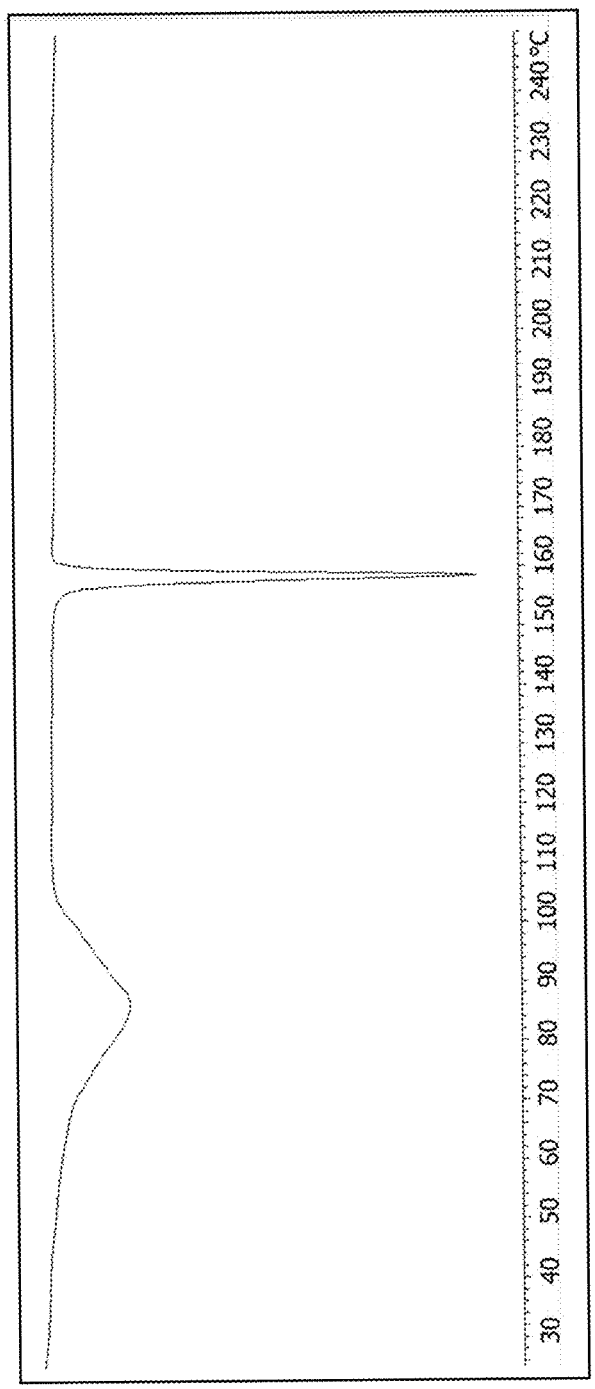

In another embodiment of the second aspect, the crystalline form (Form C) of the X-ray powder diffraction pattern is substantially the same as the X-ray powder diffraction spectrum shown in FIG. 8 at a temperature of 21-26° C.

In yet another embodiment of the second aspect, the melting peak of the crystalline form (Form C) is a broad water endotherm in the DSC trace at about 85° C.

In another embodiment of the second aspect, the crystalline form (Form C) is further characterized by the following unit cell parameters:

a=7.27 Å±0.01 Å, b=9.32 Å±0.01 Å, c=14.11 Å±0.01 Å, α=75.53°±0.01°, ß=87.03±0.01°, γ=71.48°±0.01°, Z=2.

The polymorphs of the invention may be applied in unchanged form but is more preferably incorporated into agrochemical or pharmaceutical compositions, in particular agrochemical compositions, by conventional means. Accordingly, in a third aspect, there is provided an agrochemical or pharmaceutical composition comprising the crystalline form according to the first aspect (Form B) or any of the embodiments of the first aspect and at least one acceptable, agrochemically and/or pharmaceutically, carrier or diluent. In a fourth aspect, there is provided an agrochemical or pharmaceutical composition comprising the crystalline form according to the second aspect (Form C) or any of the embodiments of the second aspect and at least one acceptable, agrochemically and/or pharmaceutically, carrier or diluent.

Figure 12:
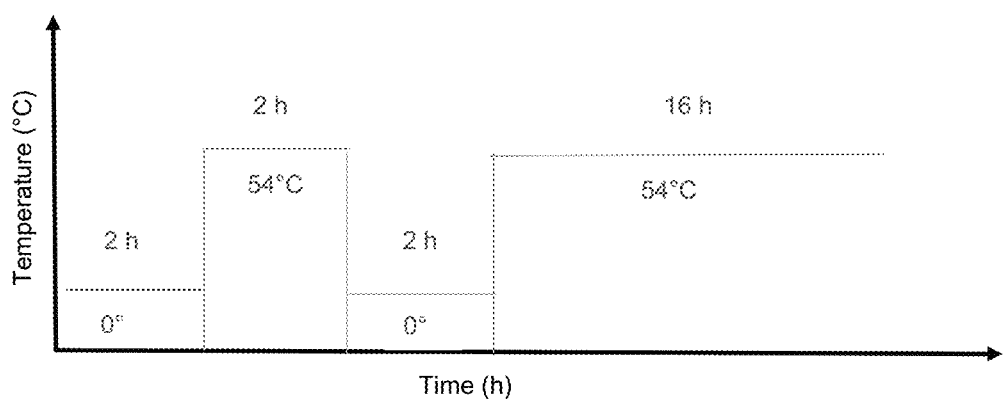

As mentioned previously, it is crucial for the successful application of an agrochemical and/or pharmaceutical formulation that the crystalline form is stable in the particular formulation environment. Flowable concentrates for seed treatment (FS) formulations were prepared for both Form A and Form B. The only difference between the two formulations was the polymorphic form used, all of the other components were identical. The formulations were tested for the crucial stability according to a temperature cycling test which is shown in FIG. 12. The formulations were analyzed under a microscope (40×) for possible crystal growth which can have detrimental consequences such as thickening and potentially solidification of the formulation which can in turn lead to blockages in application equipment, e.g. in seed coating equipment or in spray nozzles in agricultural application machinery. Pictures were taken of the formulations at (i) start (FIGS. 13a and 14a), (ii) immediately after the temperature cycling test (FIGS. 13b and 14b) and (iii) two days at room temperature (RT) after the temperature cycling test (FIGS. 13c and 14c). The pictures are shown for the formulation comprising Form A in FIGS. 13a, 13b and 13c and the pictures for the formulations comprising Form B in FIGS. 14a, 14b and 14c. One can see in FIGS. 13a and 14a that both formulations did not exhibit any crystal growth before the temperature cycling test. FIG. 13b exhibited clear crystal growth after the temperature cycling test. Storing the formulation for another two days at RT led to even further crystal growth (FIG. 13c). Surprisingly and unexpected, the same temperature cycling test showed for the formulation comprising Form B no such crystal growth, see FIGS. 14b and 14c. This is unexpected as both polymorphic forms were shown to be chemically stable in the formulations tested, i.e. no compound degradation was observed. However, Form B was found to be surprisingly resistant to crystal growth when exposed to typical storage conditions. Hence, agrochemical or pharmaceutical compositions comprising the crystalline Form B are preferred.

The agrochemical compositions comprising the polymorphic Form B or C have a very advantageous spectrum of activities for protecting animals and useful plants against attack and damage by nematodes, in particular protecting useful plants against attack and damage by nematodes.

The agrochemical compositions comprising the polymorphic Form B or C have a very advantageous spectrum of activities for protecting animals and useful plants against attack and damage by fungi, in particular protecting useful plants against attack and damage by fungi.

The agrochemical compositions comprising the polymorphic Form B or C may be used for controlling or destroying pests which occur in particular on plants, especially on useful plants and ornamentals in agriculture, in horticulture and in forests, or on organs, such as fruits, flowers, foliage, stalks, tubers, seeds or roots, of such plants, and in some cases even plant organs which are formed at a later point in time remain protected against these pests. The agrochemical compositions of the invention are preventively and/or curatively valuable active ingredients in the field of pest control, even at low rates of application, which can be used against pesticide resistant pests such as insects and fungi, and have a very favorable biocidal spectrum and are well tolerated by warm-blooded species, fish and plants.

Examples of the above mentioned nematode pests are:

Endoparasitic-, Semiendoparasitic- and Ectoparasitic nematodes, especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Eelonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Helicotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

Examples of the above mentioned fungi are:

Fungi imperfecti (e.g. *Botrytis, Pyricularia, Helminthosporium, Fusarium, Septoria, Cercospora* and *Alternaria*); Basidiomycetes (e.g. *Rhizoctonia, Hemileia, Puccinia*); the Ascomycetes classes (e.g. *Venturia* and *Erysiphe, Podosphaera, Monilinia, Uncinula*); Oomycetes classes (e.g. *Phytophthora,* Pythium, *Plasmopara*); Zygomycetes (e.g., *Rhizopus* spp.); family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal plants and *Puccinia recondita*, also known as brown rust.

Among the plants and the possible diseases of these plants protected by the method according to the present invention, mention may be made of:

wheat, as regards controlling the following seed diseases: fusaria (*Microdochium nivale* and *Fusarium roseum*), stinking smut (*Tilletia caries, Tilletia controversa* or *Tilletia indica*), septoria disease (*Septoria nodorum*) and loose smut;

wheat, as regards controlling the following diseases of the aerial parts of the plant: cereal eyespot (*Tapesia yallundae, Tapesia acuiformis*), take-all (*Gaeumannomyces graminis*), foot blight (*F. culmorum, F. graminearum*), black speck (*Rhizoctonia cerealis*), powdery mildew (*Erysiphe graminis forma* specie *tritici*), rusts (*Puccinia striiformis* and *Puccinia recondite*) and *septoria* diseases (*Septoria tritici* and *Septoria nodorum*);

wheat and barley, as regards controlling bacterial and viral diseases, for example barley yellow mosaic; —barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);

barley, as regards controlling the following diseases of the aerial parts of the plant: cereal eyespot (*Tapesia yallundae*), net blotch (*Pyrenophora teres* and *Cochliobolus sativus*), powdery mildew (*Erysiphe graminis forma* specie *hordei*), dwarf leaf rust (*Puccinia hordei*) and leaf blotch (*Rhynchosporium secalis*);

potato, as regards controlling tuber diseases (in particular *Helminthosporium solani, Phoma tuberosa, Rhizoctonia solani, Fusarium solani*), mildew (*Plrytopthora infestans*) and certain viruses (virus Y);

potato, as regards controlling the following foliage diseases: early blight (*Alternaria solani*), mildew (*Phytophthora infestans*);

cotton, as regards controlling the following diseases of young plants grown from seeds: damping-off and collar rot (*Rhizoctonia solani, Fusarium oxysporum*) and black root rot (*Thielaviopsis basicola*);

protein yielding plants, for example peas, as regards controlling the following seed diseases: anthracnose (*Ascochyta pisi, Mycosphaerella pinodes*), fusaria (*Fusarium oxysporum*), grey mould (*Botrytis cinerea*) and mildew (*Peronospora pisi*);

oil-bearing plants, for example rape, as regards controlling the following seed diseases: *Phoma lingam, Alternaria brassicae* and *Sclerotinia sclerotiorum;* corn, as regards controlling seed diseases: (*Rhizopus* sp., *Penicillium* sp., *Trichoderma* sp., *Aspergillus* sp., and *Gibber ellafujikuroi*);

flax, as regards controlling the seed disease: *Alternaria linicola;* forest trees, as regards controlling damping-off (*Fusarium oxysporum, Rhizoctonia solani*);

rice, as regards controlling the following diseases of the aerial parts: blast disease (*Magnaporthe grisea*), bordered sheath spot (*Rhizoctonia solani*);

leguminous plants, as regards controlling the following diseases of seeds or of young plants grown from seeds: damping-off and collar rot (*Fusarium oxysporum, Fusarium roseum, Rhizoctonia solani, Pythium* sp.);

leguminous plants, as regards controlling the following diseases of the aerial parts: grey mould (*Botrytis* sp.), powdery mildews (in particular *Erysiphe cichoracearum, Sphaerotheca fuliginea* and *Leveillula taurica*), fusaria (*Fusarium oxysporum, Fusarium roseum*), leaf spot (*Cladosporium* sp.), alternaria leaf spot (*Alternaria* sp.), anthracnose (*Colletotrichum* sp.), septoria leaf spot (*Septoria* sp.), black speck (*Rhizoctonia solani*), mildews (for example *Bremia lactucae, Peronospora* sp., *Pseudoperonospora* sp., *Phytophthora* sp.);

fruit trees, as regards diseases of the aerial parts: monilia disease (*Monilia fructigenae, M. laxa*), scab (*Venturia inaequalis*), powdery mildew (*Podosphaera leucotricha*); —vine, as regards diseases of the foliage: in particular grey mould (*Botrytis cinerea*), powdery mildew (*Uncinula necator*), black rot (*Guignardia biwelli*) and mildew (*Plasmopara viticola*);

beetroot, as regards the following diseases of the aerial parts: *cercospora* blight (*Cercospora beticola*), powdery mildew (*Erysiphe beticola*), leaf spot (*Ramularia beticola*).

Accordingly, in a fifth aspect, there is provided a method of protecting crops of useful plants against damages caused by nematodes or fungi, which comprises treating the plants or the locus thereof with a composition according to the third or fourth aspects or any embodiments of the third or fourth aspects, in particular treating the plants or the locus thereof with a composition according to the third aspect or any embodiments of the third aspect.

In a sixth aspect, there is provided a method of protecting plant propagation material against damages caused by nematode or fungi, which comprises treating the plant propagation material with a composition according to the third or fourth aspects or any embodiments of the third or fourth aspects, in particular treating the plant propagation material with a composition according to the third aspect or any embodiments of the third aspect.

In a seventh aspect, there is provided a method of controlling and preventing endo- and ectoparasitic nematode infestations and infections in warm-blooded animals, which comprises injecting, topically applying or orally administering a composition according to the third or fourth aspects or any embodiments of the third or fourth aspects, in particular with a composition according to the third aspect or any embodiments of the third aspect.

Furthermore, in an eighth aspect, there is provided a crystalline form according to the first and second aspect for use in protecting useful plants against damages caused by nematode pests or fungi.

By the term "plant propagation material" is meant seeds of all kinds (fruit, tubers, bulbs, grains, etc.), cuttings, cut shoots and the like.

Suitable target plants are for the compositions of the invention, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous plants, such as beans, lentils, peas or soya; oil plants, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals (such as flowers, and lawn grass or turf).

The term "plant" or "crop" are to be understood as being those which are naturally occurring, obtained by conventional methods of breeding, or obtained by genetic engineering. They include plants or crops which contain so-called output traits (e.g. improved storage stability, higher nutritional value and improved flavour).

The term "plant" or "crop" are to be understood as also including those plants or crops which have been rendered tolerant to herbicides like bromoxynil or classes of herbicides such as ALS-, EPSPS-, GS-, HPPD- and PPO-inhibitors. An example of a plant that has been rendered tolerant to imidazolinones, e.g. imazamox, by conventional methods of breeding is Clearfield® summer canola. Examples of plants that have been rendered tolerant to herbicides by genetic engineering methods include e.g. glyphosate- and glufosinate-resistant maize varieties commercially available under the trade names RoundupReady®, Herculex I® and LibertyLink®.

The term "plant" or "crop" are to be understood as including those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a plant that has been modified to express the *Bacillus thuringiensis* toxin is the Bt maize KnockOut® (Syngenta Seeds). An example of a plant comprising more than one gene that codes for insecticidal resistance and thus expresses more than one toxin is VipCot® (Syngenta Seeds). Plants or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgraSciences, Pioneer Hi-Bred International).

The rate at which the agrochemical compositions of the invention are applied will depend upon the particular type of nematode or fungi etc. to be controlled, the degree of control required and the timing and method of application and can be determined by the person skilled in the art. In general, the compositions of the invention can be applied at an application rate of between 0.005 kilograms/hectare (kg/ha) and about 5.0 kg/ha, based on the total amount of active ingredient (wherein 'active ingredient' means the polymorph Form B or C) in the composition. An application rate of between about 0.001 kg/ha and about 0.5 kg/ha is preferred, with an application rate of between about 0.01 kg/ha and 0.04 kg/ha being especially preferred.

In practice, the agrochemical compositions comprising the polymorph of Form B or C are applied as a formulation containing the various adjuvants and carriers known to or used in the industry.

These formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the polymorph ('active ingredient') with the formulation adjuvants in order to obtain formulations in the form of finely divided solids, granules, solutions, dispersions or emulsions. The active ingredient can also be formulated with other adjuvants, such as finely divided solids, mineral oils, oils of vegetable or animal origin, modified oils of vegetable or animal origin, organic solvents, water, surface-active substances or combinations thereof.

The active ingredient can also be contained in very fine microcapsules. Microcapsules contain the active ingredient in a porous carrier. This enables the active ingredient to be released into the environment in controlled amounts (e.g. slow-release). Microcapsules usually have a diameter of from 0.1 to 500 microns. They contain the active ingredient in an amount of about from 25 to 95% by weight of the capsule weight. The active ingredient can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the formulations according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, takeup enhancers, micronutrients, plasticisers, glidants, lubricants, dispersants, thickeners, antifreezes, microbicides, and liquid and solid fertilisers.

The formulations according to the invention can include an additive comprising an oil of vegetable or animal origin, a mineral oil, alkyl esters of such oils or mixtures of such oils and oil derivatives. The amount of oil additive in the formulations according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10th Edition, Southern Illinois University, 2010.

The inventive formulations generally comprise from 0.1 to 99% by weight, especially from 0.1 to 95% by weight, of polymorphs of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

| Emulsifiable concentrates: | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |
| Dusts: | |
| active ingredient: | 0.1 to 10%, preferably 0.1 to 5% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.1 to 30%, preferably 0.1 to 15% |
| solid carrier: | 99.5 to 70%, preferably 97 to 85% |

Each of the above formulations can be prepared as a package containing the polymorph Form B or C together with other ingredients of the formulation (diluents, emulsifiers, surfactants, etc.). The formulations can also be prepared by a tank mix method, in which the ingredients are obtained separately and combined at the grower site.

These formulations can be applied to the areas where control is desired by conventional methods. Dust and liquid formulations, for example, can be applied by the use of power-dusters, broom and hand sprayers and spray dusters. The formulations can also be applied from airplanes as a dust or a spray or by rope wick applications. Both solid and liquid formulations may also be applied to the soil in the locus of the plant to be treated allowing the active ingredient to penetrate the plant through the roots. The formulations of the invention may also be used for dressing applications on plant propagation material to provide protection against insect infections on the plant propagation material as well as against insects occurring in the soil. In particular, the active ingredient, i.e. polymorph Form B or C, or a composition comprising polymorph Form B or C may be applied to plant propagation material to be protected by impregnating the plant propagation material, in particular, seeds, either with a liquid formulation of the polymorph Form B or C or coating it with a solid formulation. In special cases, other types of application are also possible, for example, the specific treatment of plant cuttings or twigs serving propagation.

Suitably, the agrochemical compositions and formulations of the present invention are applied prior to disease development. Rates and frequency of use of the formulations are those conventionally used in the art and will depend on the risk of infestation by the insect pathogen.

Normally, in the management of a crop a grower would use one or more other agronomic chemicals in addition to the crystalline polymorph of the present invention. Examples of agronomic chemicals include pesticides, such as acaricides, bactericides, fungicides, herbicides, insecticides, nematicides, as well as plant nutrients and plant fertilizers.

Accordingly, the present invention provides for the use of a composition according to the present invention together with one or more pesticides, plant nutrients or plant fertilizers. The combination may also encompass specific plant traits incorporated into the plant using any means, for example conventional breeding or genetic modification.

The mixtures of the polymorph Form B or C with other active substances may also have further surprising advantages which can also be described, in a wider sense, as synergistic activity. For example, better tolerance by plants, reduced phytotoxicity, insects can be controlled in their different development stages, or better behaviour relating to production, for example grinding or mixing, storage or use.

Preferred mixtures are indicated below where the polymorph Form B or C is indicated as "I":

Compositions comprising an adjuvant include I+compounds selected from the group of substances consisting of petroleum oils.

Compositions comprising an acaricide include I+1,1-bis (4-chlorophenyl)-2-ethoxyethanol, I+2,4-dichlorophenyl benzenesulfonate, I+2-fluoro-N-methyl-N-1-naphthylacetamide, I+4-chlorophenyl phenyl sulfone, I+abamectin, I+acequinocyl, I+acetoprole, I+acrinathrin, I+aldicarb, I+aldoxycarb, I+alpha-cypermethrin, I+amidithion, I+amidoflumet, I+amidothioate, I+amiton, I+amiton hydrogen oxalate, I+amitraz, I+aramite, I+arsenous oxide, I+AVI 382, I+AZ 60541, I+azinphos-ethyl, I+azinphos-methyl, I+azobenzene, I+azocyclotin, I+azothoate, I+benomyl, I+benoxafos, I+benzoximate, I+benzyl benzoate, I+bifenazate, I+bifenthrin, I+binapacryl, I+brofenvalerate, I+bromocyclen, I+bromophos, I+bromophos-ethyl, I+bromopropylate, I+buprofezin, I+butocarboxim, I+butoxycarboxim, I+butylpyridaben, I+calcium polysulfide, I+camphechlor, I+carbanolate, I+carbaryl, I+carbofuran, I+carbophenothion, I+CGA 50'439, I+chinomethionat, I+chlorbenside, I+chlordimeform, I+chlordimeform hydrochloride, I+chlorfenapyr, I+chlorfenethol, I+chlorfenson, I+chlorfensulfide, I+chlorfenvinphos, I+chlorobenzilate, I+chloromebuform, I+chloromethiuron, I+chloropropylate, I+chlorpyrifos, I+chlorpyrifos-methyl, I+chlorthiophos, I+cinerin I, I+cinerin II, I+cinerins, I+clofentezine, I+closantel, I+coumaphos, I+crotamiton, I+crotoxyphos, I+cufraneb, I+cyanthoate, I+cyflumetofen, I+cyhalothrin, I+cyhexatin, I+cypermethrin, I+DCPM, I+DDT, I+demephion, I+demephion-O, I+demephion-S, I+demeton, I+demeton-methyl, I+demeton-O, I+demeton-O-methyl, I+demeton-S, I+demeton-S-methyl, I+demeton-S-methylsulfon, I+diafenthiuron, I+dialifos, I+diazinon, I+dichlofluanid, I+dichlorvos, I+dicliphos, I+dicofol, I+dicrotophos, I+dienochlor, I+dimefox, I+dimethoate, I+dinactin, I+dinex, I+dinex-diclexine, I+dinobuton, I+dinocap, I+dinocap-4, I+dinocap-6, I+dinocton, I+dinopenton, I+dinosulfon, I+dinoterbon, I+dioxathion, I+diphenyl sulfone, I+disulfiram, I+disulfoton, I+DNOC, I+dofenapyn, I+doramectin, I+endosulfan, I+endothion, I+EPN, I+eprinomectin, I+ethion, I+ethoatemethyl, I+etoxazole, I+etrimfos, I+fenazaflor, I+fenazaquin, I+fenbutatin oxide, I+fenothiocarb, I+fenpropathrin, I+fenpyrad, I+fenpyroximate, I+fenson, I+fentrifanil, I+fenvalerate, I+fipronil, I+fluacrypyrim, I+fluazuron, I+flubenzimine, I+flucycloxuron, I+flucythrinate, I+fluenetil, I+flufenoxuron, I+flumethrin, I+fluorbenside, I+fluvalinate, I+FMC 1137, I+formetanate, I+formetanate hydrochloride, I+formothion, I+formparanate, I+gamma-HCH, I+glyodin, I+halfenprox, I+heptenophos, I+hexadecyl cyclopropanecarboxylate, I+hexythiazox, I+iodomethane, I+isocarbophos, I+isopropyl O-(methoxyaminothiophosphoryl)salicylate, I+ivermectin, I+jasmolin I, I+jasmolin II, I+jodfenphos, I+lindane, I+lufenuron, I+malathion, I+malonoben, I+mecarbam, I+mephosfolan, I+mesulfen, I+methacrifos, I+methamidophos, I+methidathion, I+methiocarb, I+methomyl, I+methyl bromide, I+metolcarb, I+mevinphos, I+mexacarbate, I+milbemectin, I+milbemycin oxime, I+mipafox, I+monocrotophos, I+morphothion, I+moxidectin, I+naled, I+NC-184, I+NC-512, I+nifluridide, I+nikkomycins, I+nitrilacarb, I+nitrilacarb 1:1 zinc chloride complex, I+NNI-0101, I+NNI-0250, I+omethoate, I+oxamyl, I+oxydeprofos, I+oxydisulfoton, I+pp'-DDT, I+parathion, I+permethrin, I+petroleum oils, I+phenkapton, I+phenthoate, I+phorate, I+phosalone, I+phosfolan, I+phosmet, I+phosphamidon, I+phoxim, I+pirimiphos-methyl, I+polychloroterpenes, I+polynactins, I+proclonol, I+profenofos, I+promacyl, I+propargite, I+propetamphos, I+propoxur, I+prothidathion, I+prothoate, I+pyrethrin I, I+pyrethrin II, I+pyrethrins, I+pyridaben, I+pyridaphenthion, I+pyrimidifen, I+pyrimitate, I+quinalphos, I+quintiofos, I+R-1492, I+RA-17, I+rotenone, I+schradan, I+sebufos, I+selamectin, I+SI-0009, I+sophamide, I+spirodiclofen, I+spiromesifen, I+SSI-121, I+sulfiram, I+sulfluramid, I+sulfotep, I+sulfur, I+SZI-121, I+tau-fluvalinate, I+tebufenpyrad, I+TEPP, I+terbam, I+tetrachlorvinphos, I+tetradifon, I+tetranactin, I+tetrasul, I+thiafenox, I+thiocarboxime, I+thiofanox, I+thiometon, I+thioquinox, I+thuringiensin, I+triamiphos, I+triarathene, I+triazophos, I+triazuron, I+trichlorfon, I+trifenofos, I+trinactin, I+vamidothion, I+vaniliprole and I+YI-5302.

Compositions comprising an anthelmintic include I+abamectin, I+crufomate, I+doramectin, I+emamectin, I+emamectin benzoate, I+eprinomectin, I+ivermectin, I+milbemycin oxime, I+moxidectin, I+piperazine, I+selamectin, I+spinosad and I+thiophanate.

Compositions comprising an avicide include I+chloralose, I+endrin, I+fenthion, I+pyridin-4-amine and I+strychnine.

Compositions comprising a biological control agent include I+*Adoxophyes orana* GV, I+*Agrobacterium radiobacter*, I+*Amblyseius* spp., I+*Anagrapha falcifera* NPV, I+*Anagrus atomus*, I+*Aphelinus abdominalis*, I+*Aphidius colemani*, I+*Aphidoletes aphidimyza*, I+*Autographa californica* NPV, I+*Bacillus firmus*, I+*Bacillus sphaericus* Neide, I+*Bacillus thuringiensis* Berliner, I+*Bacillus thuringiensis* subsp. *aizawai*, I+*Bacillus thuringiensis* subsp. *israelensis*, I+*Bacillus thuringiensis* subsp. *japonensis*, I+*Bacillus thuringiensis* subsp. *kurstaki*, I+*Bacillus thuringiensis* subsp. *tenebrionis*, I+*Beauveria bassiana*, I+*Beauveria brongniartii*, I+*Chrysoperla carnea*, I+*Cryptolaemus montrouzieri*, I+*Cydia pomonella* GV, I+*Dacnusa sibirica*, I+*Diglyphus isaea*, I+*Encarsia formosa*, I+*Eretmocerus eremicus*, I+*Helicoverpa zea* NPV, I+*Heterorhabditis bacteriophora* and *H. megidis*, I+*Hippodamia convergens*, I+*Leptomastix dactylopii*, I+*Macrolophus caliginosus*, I+*Mamestra brassicae* NPV, I+*Metaphycus helvolus*, I+*Metarhizium anisopliae* var. *acridum*, I+*Metarhizium anisopliae* var. *anisopliae*, I+*Neodiprion sertifer* NPV and *N. lecontei* NPV, I+*Orius* spp., I+*Paecilomyces fumosoroseus*, I+*Phytoseiulus persimilis*, I+*Spodoptera exigua* multicapsid nuclear polyhedrosis virus, I+*Steinernema bibionis*, I+*Steinernema carpocapsae*, I+*Steinernema feltiae*, I+*Steinernema glaseri*, I+*Steinernema riobrave*, I+*Steinernema riobravis*, I+*Steinernema scapterisci*, I+*Steinernema* spp., I+*Trichogramma* spp., I+*Typhlodromus occidentalis* and I+*Verticillium lecanii*.

Compositions comprising a soil sterilant include I+iodomethane and methyl bromide.

Compositions comprising a chemosterilant include I+apholate, I+bisazir, I+busulfan, I+diflubenzuron, I+dimatif, I+hemel, I+hempa, I+metepa, I+methiotepa, I+methyl apholate, I+morzid, I+penfluron, I+tepa, I+thiohempa, I+thiotepa, I+tretamine and I+uredepa. Compositions comprising an insect pheromone include I+(E)-dec-5-en-1-yl acetate with (E)-dec-5-en-1-ol, I+(E)-tridec-4-en-1-yl acetate, I+(E)-6-methylhept-2-en-4-ol, I+(E,Z)-tetradeca-4,10-dien-1-yl acetate, I+(Z)-dodec-7-en-1-yl acetate, I+(Z)-hexadec-11-enal, I+(Z)-hexadec-11-en-1-yl acetate, I+(Z)-hexadec-13-en-11-yn-1-yl acetate, I+(Z)-icos-13-en-10-one, I+(Z)-tetradec-7-en-1-al, I+(Z)-tetradec-9-en-1-ol, I+(Z)-tetradec-9-en-1-yl acetate, I+(7E,9Z)-dodeca-7,9-dien-1-yl acetate, I+(9Z,11E)-tetradeca-9,11-dien-1-yl acetate, I+(9Z,12E)-tetradeca-9,12-dien-1-yl acetate, I+14-methyloctadec-1-ene, I+4-methylnonan-5-ol with 4-methylnonan-5-one, I+alpha-multistriatin, I+brevicomin, I+codlelure, I+codlemone, I+cuelure, I+disparlure, I+dodec-8-en-1-yl acetate, I+dodec-9-en-1-yl acetate, I+dodeca-8, I+10-dien-1-yl acetate, I+dominicalure, I+ethyl 4-methyloctanoate, I+eugenol, I+frontalin, I+gossyplure, I+grandlure, I+grandlure I, I+grandlure II, I+grandlure III, I+grandlure IV, I+hexalure, I+ipsdienol, I+ipsenol, I+japonilure, I+lineatin, I+litlure, I+looplure, I+medlure, I+megatomoic acid, I+methyl eugenol, I+muscalure, I+octadeca-2,13-dien-1-yl acetate, I+octadeca-3,13-dien-1-yl acetate, I+orfralure, I+oryctalure, I+ostramone, I+siglure, I+sordidin, I+sulcatol, I+tetradec-11-en-1-yl acetate, I+trimedlure, I+trimedlure A, I+trimedlure $B_1$, I+trimedlure $B_2$, I+trimedlure C and I+trunc-call.

Compositions comprising an insect repellent include I+2-(octylthio)ethanol, I+butopyronoxyl, I+butoxy(polypropylene glycol), I+dibutyl adipate, I+dibutyl phthalate, I+dibutyl succinate, I+diethyltoluamide, I+dimethyl carbate, I+dimethyl phthalate, I+ethyl hexanediol, I+hexamide, I+methoquin-butyl, I+methylneodecanamide, I+oxamate and I+picaridin.

Compositions comprising an insecticide include I+1-dichloro-1-nitroethane, I+1,1-dichloro-2,2-bis(4-ethylphenyl)ethane, I+, I+1,2-dichloropropane, I+1,2-dichloropropane with 1,3-dichloropropene, I+1-bromo-2-chloroethane, I+2,2,2-trichloro-1-(3,4-dichlorophenyl)ethyl acetate, I+2,2-dichlorovinyl 2-ethylsulfinylethyl methyl phosphate, I+2-(1,3-dithiolan-2-yl)phenyl dimethylcarbamate, I+2-(2-butoxyethoxy)ethyl thiocyanate, I+2-(4,5-dimethyl-1,3-dioxolan-2-yl)phenyl methylcarbamate, I+2-(4-chloro-3,5-xylyloxy)ethanol, I+2-chlorovinyl diethyl phosphate, I+2-imidazolidone, I+2-isovalerylindan-1,3-dione, I+2-methyl(prop-2-ynyl)aminophenyl methylcarbamate, I+2-thiocyanatoethyl laurate, I+3-bromo-1-chloroprop-1-ene, I+3-methyl-1-phenylpyrazol-5-yl dimethylcarbamate, I+4-methyl(prop-2-ynyl)amino-3,5-xylyl methylcarbamate, I+5,5-dimethyl-3-oxocyclohex-1-enyl dimethylcarbamate, I+abamectin, I+acephate, I+acetamiprid, I+acethion, I+acetoprole, I+acrinathrin, I+acrylonitrile, I+alanycarb, I+aldicarb, I+aldoxycarb, I+aldrin, I+allethrin, I+allosamidin, I+allyxycarb, I+alpha-cypermethrin, I+alpha-ecdysone, I+aluminium phosphide, I+amidithion, I+amidothioate, I+aminocarb, I+amiton, I+amiton hydrogen oxalate, I+amitraz, I+anabasine, I+athidathion, I+AVI 382, I+AZ 60541, I+azadirachtin, I+azamethiphos, I+azinphos-ethyl, I+azinphos-methyl, I+azothoate, I+*Bacillus thuringiensis* delta endotoxins, I+barium hexafluorosilicate, I+barium polysulfide, I+barthrin, I+Bayer 22/190, I+Bayer 22408, I+bendiocarb, I+benfuracarb, I+bensultap, I+beta-cyfluthrin, I+beta-cypermethrin, I+bifenthrin, I+bioallethrin, I+bioallethrin S-cyclopentenyl isomer, I+bioethanomethrin, I+biopermethrin, I+bioresmethrin, I+bis(2-chloroethyl) ether, I+bistrifluron, I+borax, I+brofenvalerate, I+bromfenvinfos, I+bromocyclen, I+bromo-DDT, I+bromophos, I+bromophos-ethyl, I+bufencarb, I+buprofezin, I+butacarb, I+butathiofos, I+butocarboxim, I+butonate, I+butoxycarboxim, I+butylpyridaben, I+cadusafos, I+calcium arsenate, I+calcium cyanide, I+calcium polysulfide, I+camphechlor, I+carbanolate, I+carbaryl, I+carbofuran, I+carbon disulfide, I+carbon tetrachloride, I+carbophenothion, I+carbosulfan, I+cartap, I+cartap hydrochloride, I+cevadine, I+chlorbicyclen, I+chlordane, I+chlordecone, I+chlordimeform, I+chlordimeform hydrochloride, I+chlorethoxyfos, I+chlorfenapyr, I+chlorfenvinphos, I+chlorfluazuron, I+chlormephos, I+chloroform, I+chloropicrin, I+chlorphoxim, I+chlorprazophos, I+chlorpyrifos, I+chlorpyrifos-methyl, I+chlorthiophos, I+chromafenozide, I+cinerin I, I+cinerin II, I+cinerins, I+cis-resmethrin, I+cismethrin, I+clocythrin, I+cloethocarb, I+closantel, I+clothianidin, I+copper acetoarsenite, I+copper arsenate, I+copper oleate, I+coumaphos, I+coumithoate, I+crotamiton, I+crotoxyphos, I+crufomate, I+cryolite, I+CS 708, I+cyanofenphos, I+cyanophos, I+cyanthoate, I+cyclethrin, I+cycloprothrin, I+cyfluthrin, I+cyhalothrin, I+cypermethrin, I+cyphenothrin, I+cyromazine, I+cythioate, I+d-limonene, I+d-tetramethrin, I+DAEP, I+dazomet, I+DDT, I+decarbofuran, I+deltamethrin, I+demephion, I+demephion-O, I+demephion-S, I+demeton, I+demeton-methyl, I+demeton-O, I+demeton-O-methyl, I+demeton-S, I+demeton-S-methyl, I+demeton-S-methylsulphon, I+diafenthiuron, I+dialifos, I+diamidafos, I+diazinon, I+dicapthon, I+dichlofenthion, I+dichlorvos, I+dicliphos, I+dicresyl, I+dicrotophos, I+dicyclanil, I+dieldrin, I+diethyl 5-methylpyrazol-3-yl phosphate, I+diflubenzuron, I+dilor, I+dimefluthrin, I+dimefox, I+dimetan, I+dimethoate, I+dimethrin, I+dimethylvinphos, I+dimetilan, I+dinex, I+dinex-diclexine, I+dinoprop, I+dinosam, I+dinoseb, I+dinotefuran, I+diofenolan, I+dioxabenzofos, I+dioxacarb, I+dioxathion, I+disulfoton, I+dithicrofos, I+DNOC, I+doramectin, I+DSP, I+ecdysterone, I+EI 1642, I+emamectin, I+emamectin benzoate, I+EMPC, I+empenthrin, I+endosulfan, I+endothion, I+endrin, I+EPBP, I+EPN, I+epofenonane, I+eprinomectin, I+esfenvalerate, I+etaphos, I+ethiofencarb, I+ethion, I+ethiprole, I+ethoate-methyl, I+ethoprophos, I+ethyl formate, I+ethyl-DDD, I+ethylene dibromide, I+ethylene dichloride, I+ethylene oxide, I+etofenprox, I+etrimfos, I+EXD, I+famphur, I+fenamiphos, I+fenazaflor, I+fenchlorphos, I+fenethacarb, I+fenfluthrin, I+fenitrothion, I+fenobucarb, I+fenoxacrim, I+fenoxycarb, I+fenpirithrin, I+fenpropathrin, I+fenpyrad, I+fensulfothion, I+fenthion, I+fenthion-ethyl, I+fenvalerate, I+fipronil, I+flonicamid, I+flubendiamide, I+flucofuron, I+flucycloxuron, I+flucythrinate, I+fluenetil, I+flufenerim, I+flufenoxuron, I+flufenprox, I+flumethrin, I+fluvalinate, I+FMC 1137, I+fonofos, I+formetanate, I+formetanate hydrochloride, I+formothion, I+formparanate, I+fosmethilan, I+fospirate, I+fosthiazate, I+fosthietan, I+furathiocarb, I+furethrin, I+gamma-cyhalothrin, I+gamma-HCH, I+guazatine, I+guazatine acetates, I+GY-81, I+halfenprox, I+halofenozide, I+HCH, I+HEOD, I+heptachlor, I+heptenophos, I+heterophos, I+hexaflumuron, I+HHDN, I+hydramethylnon, I+hydrogen cyanide, I+hydroprene, I+hyquincarb, I+imidacloprid, I+imiprothrin, I+indoxacarb, I+iodomethane, I+IPSP, I+isazofos, I+isobenzan, I+isocarbophos, I+isodrin, I+isofenphos, I+isolane, I+isoprocarb, I+isopropyl O-(methoxy-aminothiophosphoryl)salicylate, I+isoprothiolane, I+isothioate, I+isoxathion, I+ivermectin, I+jasmolin I, I+jasmolin II, I+jodfenphos, I+juvenile hormone I, I+juvenile hormone II, I+juvenile hormone III, I+kelevan, I+kinoprene, I+lambda-cyhalothrin, I+lead arsenate, I+lepimectin, I+leptophos, I+lindane, I+lirimfos, I+lufenuron, I+lythidathion, I+m-cumenyl methylcarbamate, I+magnesium phosphide, I+malathion, I+malonoben, I+mazidox, I+mecarbam, I+mecarphon, I+menazon, I+mephosfolan, I+mercurous chloride, I+mesulfenfos, I+metaflumizone, I+metam, I+metam-potassium, I+metam-sodium, I+methacrifos, I+methamidophos, I+methanesulfonyl fluoride, I+methidathion, I+methiocarb, I+methocrotophos, I+methomyl, I+methoprene, I+methoquin-butyl, I+methothrin, I+methoxychlor, I+methoxyfenozide, I+methyl bromide, I+methyl isothiocyanate, I+methylchloroform, I+methylene chloride, I+metofluthrin, I+metolcarb, I+metoxadiazone, I+mevinphos, I+mexacarbate, I+milbemectin, I+milbemycin oxime, I+mipafox, I+mirex, I+monocrotophos, I+morphothion, I+moxidectin, I+naftalofos, I+naled, I+naphthalene, I+NC-170, I+NC-184, I+nicotine, I+nicotine sulfate, I+nifluridide, I+nitenpyram, I+nithiazine, I+nitrilacarb, I+nitrilacarb 1:1 zinc chloride complex, I+NNI-0101, I+NNI-0250, I+nornicotine, I+novaluron, I+noviflumuron, I+O-5-dichloro-4-iodophenyl O-ethyl ethylphosphonothioate, I+O,O-diethyl O-4-methyl-2-oxo-2H-chromen-7-yl phosphorothioate, I+O,O-diethyl O-6-methyl-2-propylpyrimidin-4-yl phosphorothioate, I+O,O,O',O'-tetrapropyl dithiopyrophosphate, I+oleic acid, I+omethoate, I+oxamyl, I+oxydemeton-methyl, I+oxydeprofos, I+oxydisulfoton, I+pp'-DDT, I+para-dichlorobenzene, I+parathion, I+parathion-methyl, I+penfluron, I+pentachlorophenol, I+pentachlorophenyl laurate, I+permethrin, I+petroleum oils, I+PH 60-38, I+phenkapton, I+phenothrin, I+phenthoate, I+phorate+TX, I+phosalone, I+phosfolan, I+phosmet, I+phosnichlor, I+phosphamidon, I+phosphine, I+phoxim, I+phoxim-methyl, I+pirimetaphos, I+pirimicarb, I+pirimiphos-ethyl, I+pirimiphos-methyl, I+polychlorodicyclopentadiene isomers, I+polychloroterpenes, I+potassium arsenite, I+potassium thiocyanate, I+prallethrin, I+precocene I, I+precocene II, I+precocene III, I+primidophos, I+profenofos, I+profluthrin, I+promacyl, I+promecarb, I+propaphos, I+propetamphos, I+propoxur, I+prothidathion, I+prothiofos, I+prothoate, I+protrifenbute, I+pymetrozine, I+pyraclofos, I+pyrazophos, I+pyresmethrin, I+pyrethrin I, I+pyrethrin II, I+pyrethrins, I+pyridaben, I+pyridalyl, I+pyridaphenthion, I+pyrimidifen, I+pyrimitate, I+pyriproxyfen, I+quassia, I+quinalphos, I+quinalphos-methyl, I+quinothion, I+quintiofos, I+R-1492, I+rafoxanide, I+resmethrin, I+rotenone, I+RU 15525, I+RU 25475, I+ryania, I+ryanodine, I+sabadilla, I+schradan, I+sebufos, I+selamectin, I+SI-0009, I+SI-0205, I+SI-0404, I+SI-0405, I+silafluofen, I+SN 72129, I+sodium arsenite, I+sodium cyanide, I+sodium fluoride, I+sodium hexafluorosilicate, I+sodium pentachlorophenoxide, I+sodium selenate, I+sodium thiocyanate, I+sophamide, I+spinosad, I+spiromesifen, I+spirotetrmat, I+sulcofuron, I+sulcofuron-sodium, I+sulfluramid, I+sulfotep, I+sulfuryl fluoride, I+sulprofos, I+tar oils, I+tau-fluvalinate, I+tazimcarb, I+TDE, I+tebufenozide, I+tebufenpyrad, I+tebupirimfos, I+teflubenzuron, I+tefluthrin, I+temephos, I+TEPP, I+terallethrin, I+terbam, I+terbufos, I+tetrachloroethane, I+tetrachlorvinphos, I+tetramethrin, I+theta-cypermethrin, I+thiacloprid, I+thiafenox, I+thiamethoxam, I+thicrofos, I+thiocarboxime, I+thiocyclam, I+thiocyclam hydrogen oxalate, I+thiodicarb, I+thiofanox, I+thiometon, I+thionazin, I+thiosultap, I+thiosultap-sodium, I+thuringiensin, I+tolfenpyrad, I+tralomethrin, I+transfluthrin, I+transpermethrin, I+triamiphos, I+triazamate, I+triazophos, I+triazuron, I+trichlorfon, I+trichlormetaphos-3, I+trichloronat, I+trifenofos, I+triflumuron, I+trimethacrb, I+triprene, I+vamidothion, I+vaniliprole, I+veratridine, I+veratrine, I+XMC, I+xylylcarb, I+YI-5302, I+zeta-cypermethrin, I+zetamethrin, I+zinc phosphide, I+zolaprofos and ZXI 8901, I+cyantraniliprole, I+chlorantraniliprole, I+cyenopyrafen, I+cyflumetofen, I+pyrifluquinazon, I+spinetoram, I+spirotetramat, I+sulfoxaflor, I+flufiprole, I+meperfluthrin, I+tetramethylfluthrin, I+triflumezopyrim.

Compositions comprising a molluscicide include I+bis (tributyltin) oxide, I+bromoacetamide, I+calcium arsenate, I+cloethocarb, I+copper acetoarsenite, I+copper sulfate, I+fentin, I+ferric phosphate, I+metaldehyde, I+methiocarb, I+niclosamide, I+niclosamide-olamine, I+pentachlorophenol, I+sodium pentachlorophenoxide, I+tazimcarb, I+thiodicarb, I+tributyltin oxide, I+trifenmorph, I+trimethacarb, I+triphenyltin acetate and triphenyltin hydroxide, I+pyriprole. Compositions comprising a nematicide include I+AKD-3088, I+1,2-dibromo-3-chloropropane, I+1,2-dichloropropane, I+1,2-dichloropropane with 1,3-dichloropropene, I+1,3-dichloropropene, I+3,4-dichlorotetrahydrothiophene 1,1-dioxide, I+3-(4-chlorophenyl)-5-methylrhodanine, I+5-methyl-6-thioxo-1,3,5-thiadiazinan-3-ylacetic acid, I+6-isopentenylaminopurine, I+abamectin, I+acetoprole, I+alanycarb, I+aldicarb, I+aldoxycarb, I+AZ 60541, I+benclothiaz, I+benomyl, I+butylpyridaben, I+cadusafos, I+carbofuran, I+carbon disulfide, I+carbosulfan, I+chloropicrin, I+chlorpyrifos, I+cloethocarb, I+cytokinins, I+dazomet, I+DBCP, I+DCIP, I+diamidafos, I+dichlofenthion, I+dicliphos, I+dimethoate, I+doramectin, I+emamectin, I+emamectin benzoate, I+eprinomectin, I+ethoprophos, I+ethylene dibromide, I+fenamiphos, I+fenpyrad, I+fensulfothion, I+fosthiazate, I+fosthietan, I+furfural, I+GY-81, I+heterophos, I+iodomethane, I+isamidofos, I+isazofos, I+ivermectin, I+kinetin, I+mecarphon, I+metam, I+metam-potassium, I+metam-sodium, I+methyl bromide, I+methyl isothiocyanate, I+milbemycin oxime, I+moxidectin, I+*Myrothecium verrucaria* composition, I+NC-184, I+oxamyl, I+phorate, I+phosphamidon, I+phosphocarb, I+sebufos, I+selamectin, I+spinosad, I+terbam, I+terbufos, I+tetrachlorothiophene, I+thiafenox, I+thionazin, I+triazophos, I+triazuron, I+xylenols, I+YI-5302 and zeatin, I+fluensulfone.

Compositions comprising a synergist include I+2-(2-butoxyethoxy)ethyl piperonylate, I+benzodioxol-5-yl)-3-hexylcyclohex-2-enone, I+farnesol with nerolidol, I+MB-599, I+MGK 264, I+piperonyl butoxide, I+piprotal, I+propyl isomer, I+S421, I+sesamex, I+sesasmolin and I+sulfoxide.

Compositions comprising an animal repellent include I+anthraquinone, I+chloralose, I+copper naphthenate, I+copper oxychloride, I+diazinon, I+dicyclopentadiene, I+guazatine, I+guazatine acetates, I+methiocarb, I+pyridin-4-amine, I+thiram, I+trimethacarb, I+zinc naphthenate and I+ziram.

Further compositions include I+Brofluthrinate, I+Cycloxaprid, I+Diflovidazine, I+Flometoquin, I+Fluhexafon, I+Guadipyr, I+Plutella xylostella Granulosis virus, I+*Cydia pomonella Granulosis* virus, I+Heroin, I+Imicyafos, I+Heliothis virescens Nucleopolyhedrovirus, I+Heliothis punctigera Nucleopolyhedrovirus, I+*Helicoverpa armigera* Nucleopolyhedrovirus, I+*Helicoverpa zea* Nucleopolyhedrovirus, I+*Spodoptera frugiperda* Nucleopolyhedrovirus, I+Plutella xylostella Nucleopolyhedrovirus, I+Pasteuria nishizawae, I+p-cymene, I+Pyflubumide, I+Pyrafluprole, I+pyrethrum, I+QRD 420, I+QRD 452, I+QRD 460, I+Terpenoid blends, I+Terpenoids, I+Tetraniliprole, and I+α-terpinene.

Composition also include mixtures of the polymorph and an active substance referenced by a code, such as I+code AE 1887196 (BSC-BX60309), I+code NNI-0745 GR, I+code IKI-3106, I+code JT-L001, I+code ZNQ-08056, I+code IPPA152201, I+code HNPC-A9908 (CAS: [660411-21-2]), I+code HNPC-A2005 (CAS: [860028-12-2]), I+code JS118, I+code ZJ0967, I+code ZJ2242, I+code JS7119 (CAS: [929545-74-4]), I+code SN-1172, I+code HNPC-A9835, I+code HNPC-A9955, I+code HNPC-A3061, I+code Chuanhua 89-1, I+code IPP-10, I+code ZJ3265, I+code JS9117, I+code SYP-9080, I+code ZJ3757, I+code ZJ4042, I+code ZJ4014, I+code ITM-121, I+code DPX-RAB55 (DKI-2301), I+code Me5382, I+code NC-515, I+code NA-89, I+code MIE-1209, I+code MCI-8007, I+code BCS-CL73507, I+code S-1871, I+code DPX-RDS63, and I+code AKD-1193.

Whilst compositions comprising the polymorph Form B or C and another insecticide etc. are explicitly disclosed above, the skilled person will appreciate that the invention extends to three-way, and further multiple combinations comprising the above two-way mixtures.

For the avoidance of doubt, even if not explicitly stated above, the mixing partners may also be in the form of any suitable agrochemically acceptable ester or salt, as mentioned e.g. in The Pesticide Manual, Fifteenth Edition, British Crop Protection Council, 2009.

The weight ratio of the polymorph Form B or C and another insecticide is generally between 1000:1 and 1:100, more preferably between 500:1 and 1:100, for example between 250:1 and 1:66, between 125:1 and 1:33, between 100:1 and 1:25, between 66:1 and 1:10, between 33:1 and 1:5 and between 8:1 and 1:3.

DESCRIPTION OF THE DRAWINGS

FIG. 1 shows the predicted powder X-ray diffraction pattern of Form A.

FIG. 2 shows the measured powder X-ray diffraction pattern of Form A.

FIG. 3 shows a DSC (DIFFERENTIAL SCANNING CALORIMETRY) trace of Form A.

FIG. 4 shows the predicted powder X-ray diffraction pattern of Form B.

FIG. 5 shows the measured powder X-ray diffraction pattern of Form B.

FIG. 6 shows a DSC (DIFFERENTIAL SCANNING CALORIMETRY) trace of Form B.

FIG. 7 shows the predicted powder X-ray diffraction pattern of Form C.

FIG. 8 shows the measured powder X-ray diffraction pattern of Form C.

FIG. 9 shows a DSC (DIFFERENTIAL SCANNING CALORIMETRY) trace of Form C.

FIG. 10 shows the measured powder X-ray diffraction pattern of Form D.

FIG. 11 shows a DSC (DIFFERENTIAL SCANNING CALORIMETRY) trace of Form D.

FIG. 12 shows the temperature cycling test to evaluate crystal growth.

FIGS. 13*a*, 13*b*, 13*c*: FIG. 13*a* is a picture taken with a microscope (40×) of a formulation with Form A at the start of the temperature cycling, FIG. 13*b* after the temperature cycling and FIG. 13*c* after the temperature cycling and storage at room temperature for two days.

FIGS. 14*a*, 14*b*, 14*c*: FIG. 14*a* is a picture taken with a microscope (40×) of a formulation with Form B at the start of the temperature cycling, FIG. 14*b* after the temperature cycling and FIG. 14*c* after the temperature cycling and storage at room temperature for two days.

EXPERIMENTAL

1. Preparation of Polymorphs

1.1 Form A

Methods for preparing Form A have been disclosed in WO2015/003951 (Example P5). An example for preparing Form A is as follows:

A solution of (1S,2S)-2-(2,4-dichlorophenyl)cyclobutanamine in toluene (339 g, 0.40 mol) is added to solid NaHCO$_3$ (47 g, 0.56 mol). Water (140 g, 7.79 mol) is then added to the reaction mixture and the mixture is heated to Ti=50° C. (T$_i$=internal temperature in the vessel). Subsequently, a solution of 2-(trifluoromethyl)pyridine-3-carbonyl chloride in toluene (247 g, 0.42 mol) is added over 53 minutes at Ti=50° C. to the reaction mixture. Once complete conversion is achieved the reaction mixture is heated to Ti=70° C. and stirred for 20 minutes at this temperature. After phase separation the organic phase is extracted with water (201 g, 11.1 mol) at Ti=80° C. Subsequent to the phase separation the organic phase is concentrated to a ca. 35% solution methyl cyclohexane (140 g, 1.4 mol) is then added over 20 minutes to the concentrated organic phase at Ti=80° C. The reaction mixture is then cooled to Ti=5° C. over 2.5 h whereas seeds are added at Ti=72° C. (crystallization works also without seeding). The reaction mixture is stirred for 30 minutes once the reaction mixture reached a Ti of 5° C. before the suspension is filtered, washed with methyl cyclohexane (200 g, 2.0 mol) and dried at elevated temperature under reduced pressure to isolate N-[(1S,2S)-2-(2,4-dichlorophenyl)cyclobutyl]-2-(trifluoromethyl) pyridine-3-carboxamide (141.6 g).

FT-IR 3282, 3077, 2981, 2952, 1650, 1593, 1543, 1473, 1353, 1187, 1138, 1074, 1066, 1054 cm$^{-1}$

1.2 Form B

Form A was dissolved in 10% water/methanol in a HPLC vial. The solvent was allowed to evaporate at room temperature.

An alternative method is as follows:

0.02 g of Form A was weighed into a HPLC vial and 0.3 ml 50% water/methanol was added. The sample was left stirring at 25° C. for a week and crystals of Form B were obtained.

Another alternative method is as follows:

Form A of N-[(1S,2S)-2-(2,4-dichlorophenyl)cyclobutyl]-2-(trifluoromethyl) pyridine-3-carboxamide (80 g) was dissolved in a mixture of acetone (240 g, 4.1 mol) and water (80 g, 4.4 mol) at Ti=55° C. (T$_i$=temperature inside the vessel). The mixture was then cooled to Ti=8° C. and seed crystals were added at Ti=29° C. Water (86 g, 4.8 mol) was added over 60 minutes to the reaction mixture once the reaction mixture reached a temperature of 8° C. The reaction mixture was stirred for 30 minutes after adding another aliquot of water (174 g, 9.7 mol) over 1 h. Subsequently, the final aliquot of water (340 g, 18.9 mol) was added and the suspension was stirred for 80 minutes. The suspension was filtered and the filter cake was washed with water (2×80 g, 4.) before it was dried under reduced pressure at 35° C. to yield the monohydrate of N-[(1S,2S)-2-(2,4-dichlorophenyl)cyclobutyl]-2-(trifluoromethyl) pyridine-3-carboxamide (94.6 g).

$^1$H NMR (400 MHz, CDCl$_3$) δ 8.65 (dd, J=4.6 Hz, J=1.2 Hz, 1H), 7.60-7.58 (m, 1H), 7.47-7.44 (m, 1H), 7.41-7.40 (m, 1H), 7.33-7.25 (m, 2H), 5.54 (br d, J=7.8 Hz, 1H), 5.03 (quin, J=7.3 Hz, 1H), 4.24 (q, J=7.8 Hz, 1H), 2.65-2.56 (m, 1H), 2.44-2.28 (m, 2H), 2.10-2.01 (m, 1H).

FT-IR 3403, 3232, 3079, 2948, 1660, 1645, 1593, 1575, 1471, 1326, 1186, 1126, 1076, 1054 cm'.

1.3 Form C

Cis-N-[2-(2,4-dichlorophenyl)cyclobutyl]-2-(trifluoromethyl)pyridine-3-carboxamide racemate (preparation method has been disclosed in WO2013/143811) was dissolved in a primary solvent (methanol, acetone or acetonitrile) in a vial and water was added to precipitate the compound. The suspension was then temperature cycled 10 to 50° C., cooled to room temperature (natural cooling) and left for 48 hours before crystals were obtained.

1.4 Form D

Cis-N-[2-(2,4-dichlorophenyl)cyclobutyl]-2-(trifluoromethyl)pyridine-3-carboxamide which is a racemate of the two enantiomers N-[(1S,2S)-2-(2,4-dichlorophenyl)cyclobutyl]-2-(trifluoromethyl)pyridine-3-carboxamide and N-[(1R,2R)-2-(2,4-dichlorophenyl)cyclobutyl]-2-(trifluoromethyl)pyridine-3-carboxamide can be prepared as described in WO2013/143811 where cis-N-[2-(2,4-dichlorophenyl)cyclobutyl]-2-(trifluoromethyl)pyridine-3-carboxamide is exemplified in Table 57, example 57.011.

2. Characterization of Polymorphs

Figure 2:
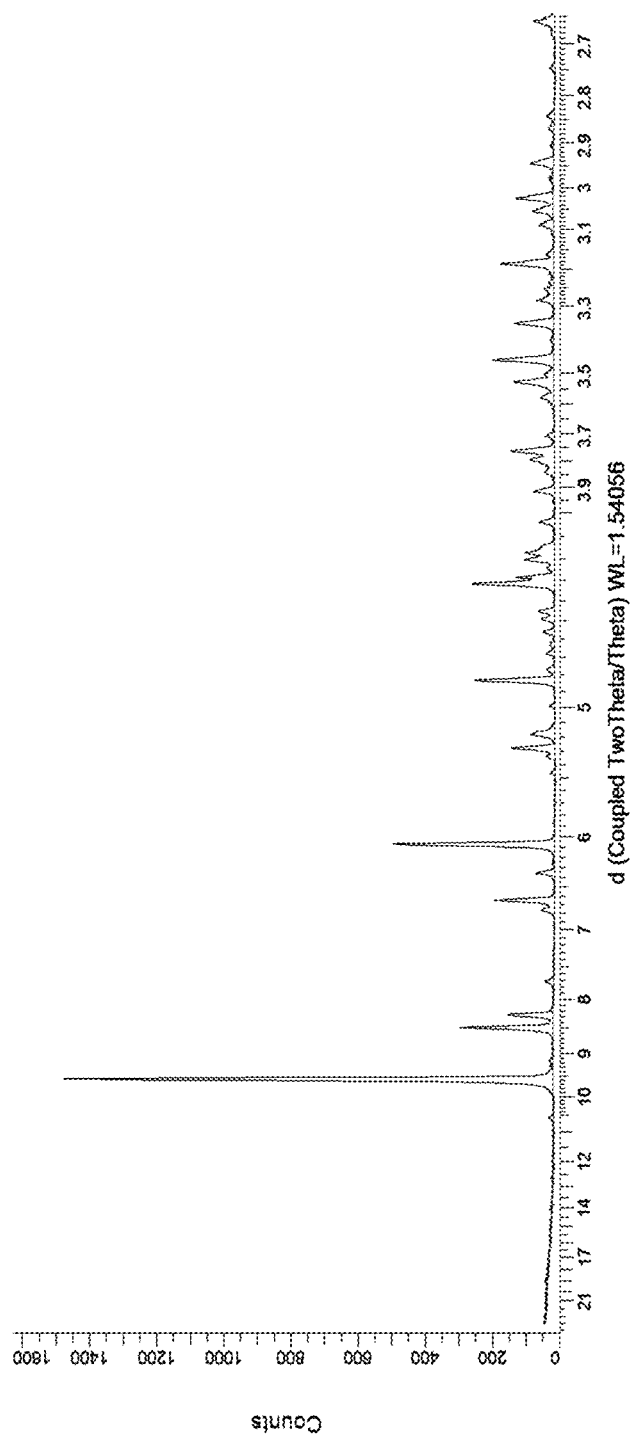
Figure 3:
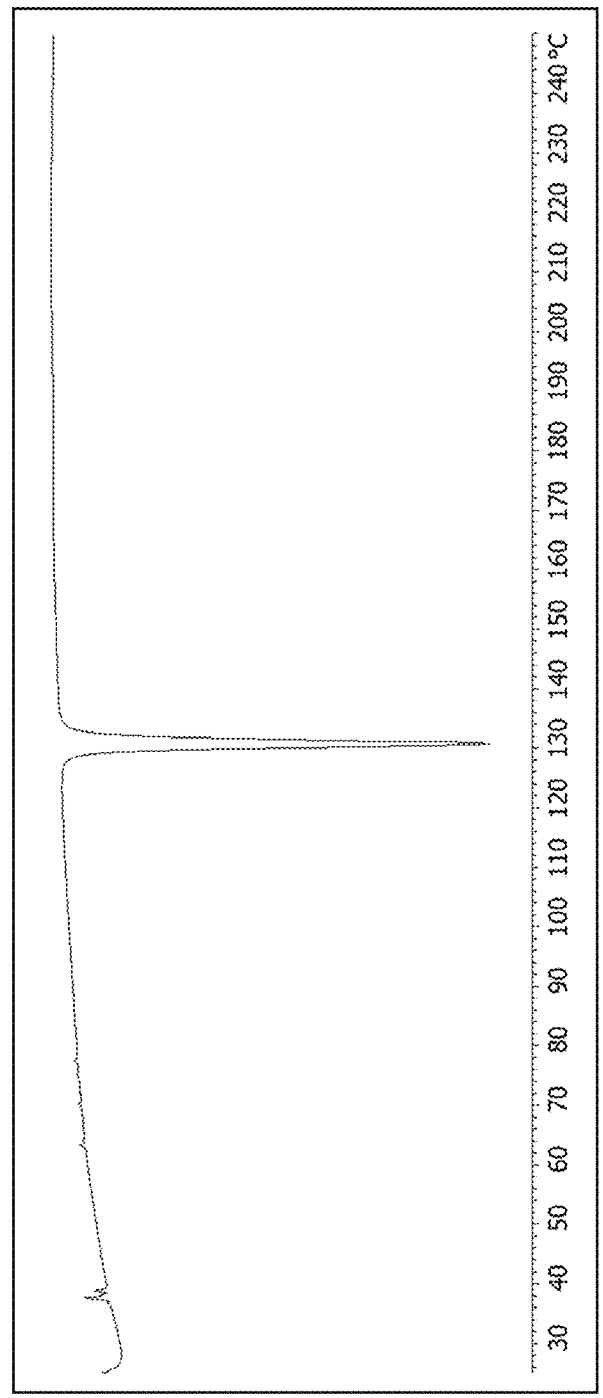

2.1 Experimental Conditions:

Powder X-Ray Diffraction Analysis (pXRD):

The powder X-ray diffraction analysis of solid material was carried out using the Bruker D8 powder diffractometer at room temperature and at relative humidities above 40%. Samples were mounted in Perspex sample holders and the samples flattened. The sample holder was rotated and X-rays were collected from 4° to 34° 2-theta, with a scan time of 25 to 30 minutes depending on the pattern intensity. Measured powder X-ray diffraction patterns for the polymorphs Form A, B and C are shown in FIGS. 2, 5 and 8, respectively.

Single Crystal Intensity Data:

Form A: Single crystal intensity data was collected on an Oxford Xcalibar PX Ultra diffractometer using Cu Kα radiation (λ=1.5418 Å) with a graphite monochromator. The crystal was mounted in NVH oil at 100 K for data collection. The data was solved using the CRYSTALS software package. This data was used to produce a predicted powder X-ray diffraction pattern for the polymorph Form A (FIG. 1).

Figure 4:
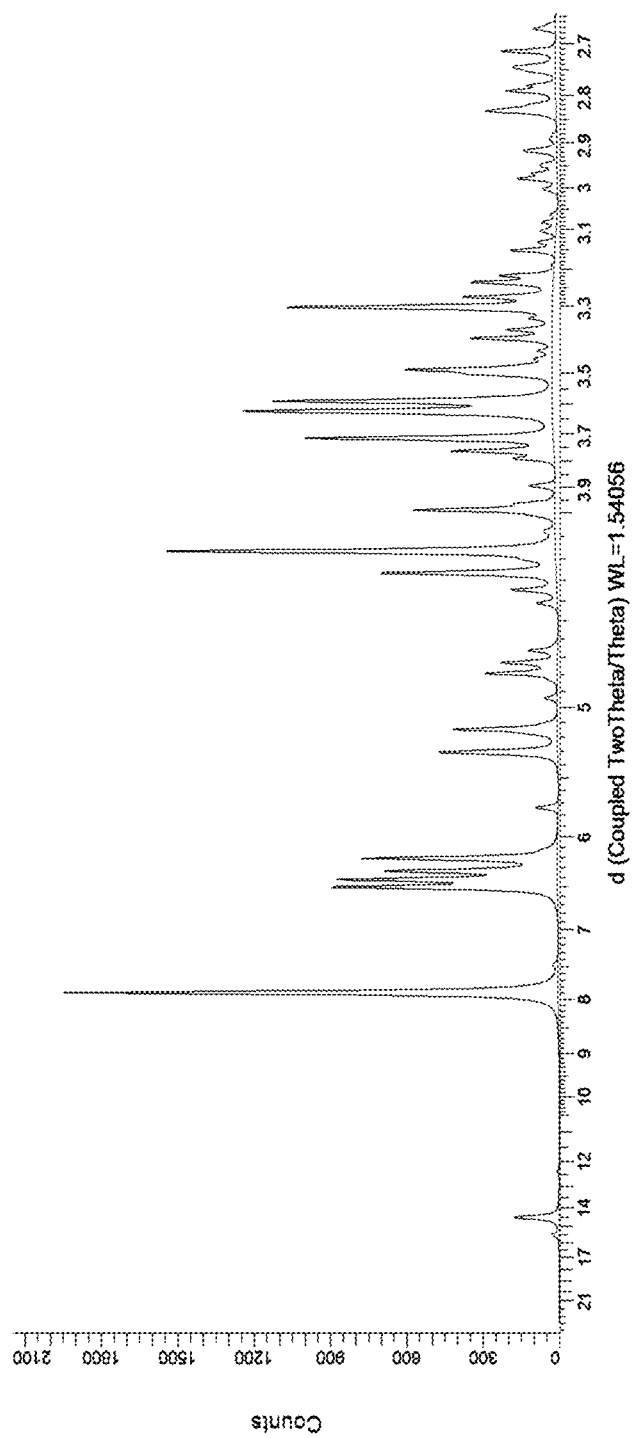

Form B: Single crystal intensity data was collected on an Oxford Xcalibar PX Ultra diffractometer using Cu Kα radiation (λ=1.5418 Å) with a graphite monochromator. The crystal was mounted in NVH oil at 298 K for data collection. The data was solved using the CRYSTALS software package. This data was used to produce a predicted powder X-ray diffraction pattern for the polymorph Form B (FIG. 4).

Figure 7:
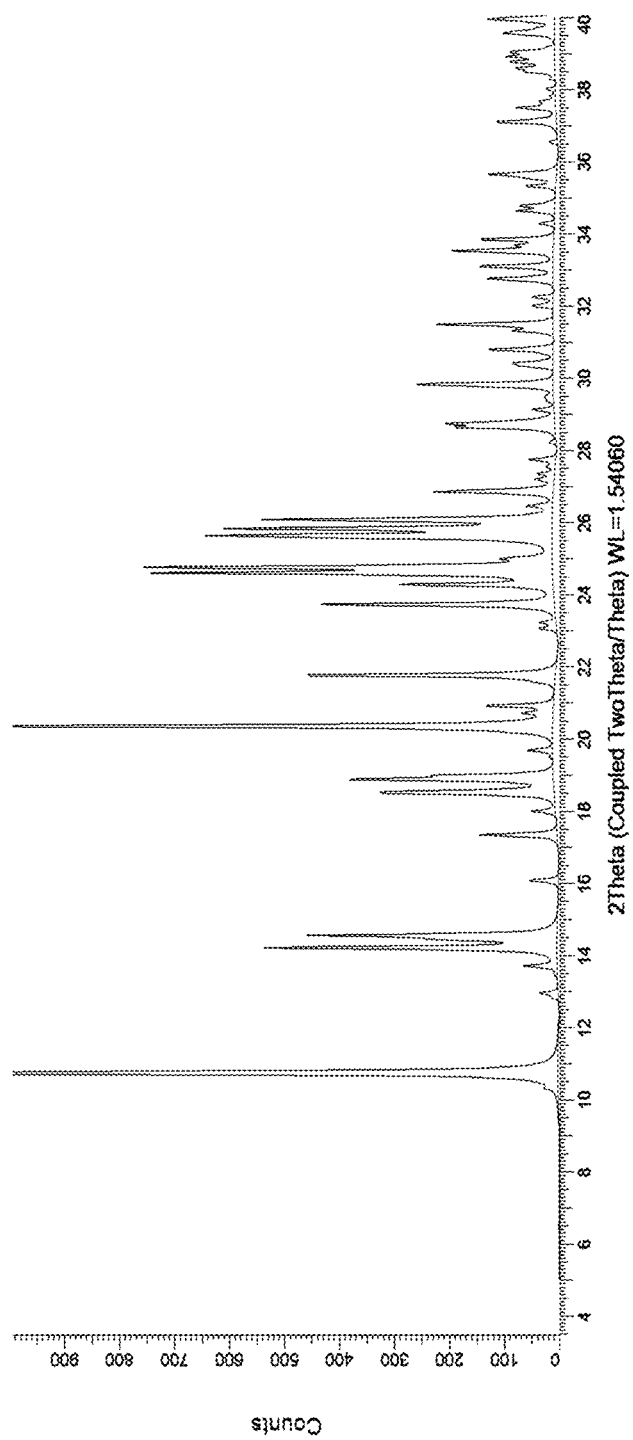

Form C: Single crystal intensity data was collected on an Rigaku XtaLAB SuperNova diffractometer using Cu Kα radiation (λ=1.5418 Å) with a graphite monochromator. The crystal was mounted in NVH oil at 100K for data collection. The data was solved using the CRYSTALS software package. This data was used to produce a predicted powder X-ray diffraction pattern for the polymorph Form C (FIG. 7).

Differential Scanning Calorimetry (DSC):

DSC was carried out using a Mettler Toledo DSC1. A sample loading of around 5 mg was used and this was heated from 25° C. to 250° C. at a rate of 10° C./minute. The lid of the DSC crucible was pierced to allow the escape of any gas formed during the heating of the sample.

2.2 Form A a) pXRD

The powder X-ray diffraction pattern of Form A is shown in FIG. 2.

TABLE 1

2-Theta and d-spacing values measured for Form A:

| 2-Theta | d |
|---|---|
| 9.3 | 9.5 |
| 10.4 | 8.5 |
| 10.7 | 8.3 |
| 13.1 | 6.8 |
| 13.3 | 6.6 |
| 14.0 | 6.3 |
| 14.6 | 6.1 |
| 16.8 | 5.3 |
| 17.2 | 5.1 |
| 18.3 | 4.8 |
| 20.6 | 4.3 |
| 20.7 | 4.3 | b) Single Crystal Unit Cell Parameters

TABLE 2

Crystallographic data for Form A

| | |
|---|---|
| Unit cell volume (Å$^3$) | 3382.98 |
| Calculated density (g/cm$^3$) | 1.598 |
| Space Group | P2$_1$2$_1$2$_1$ |
| a (Å) | 9.56 |
| b (Å) | 18.37 |
| c (Å) | 19.27 |
| α | 90 |
| β | 90 |
| γ | 90 |
| Z | 8 |
| Z' | 2 |

2.3 Form B:

a) pXRD

The X-ray powder diffraction pattern of Form B is shown in FIG. 5.

TABLE 3

2-Theta and d-spacing values measured for Form B:

| 2-Theta | d |
|---|---|
| 6.1-5.9 | 14.5-15.00 |
| 11.2-11.0 | 7.9-8.04 |
| 14.0 | 6.3 |
| 16.7 | 5.3 |
| 17.2-17.00 | 5.1-5.2 |
| 18.5 | 4.8 |
| 20.8 | 4.3 |
| 21.3 | 4.2 |
| 22.3 | 4.0 |
| 23.6 | 3.8 |
| 23.9-23.7 | 3.7-3.8 |
| 24.5 | 3.6 | b) Single Crystal Unit Cell Parameters

TABLE 4

Crystallographic data for Form B:

| | |
|---|---|
| Unit cell volume (Å$^3$) | 1805.56 |
| Calculated density (g/cm$^3$) | 1.497 |
| Space Group | P2$_1$ |
| a (Å) | 15.52 |
| b (Å) | 7.24 |
| c (Å) | 16.64 |
| α | 90 |
| β | 105.03 |

TABLE 4-continued

Crystallographic data for Form B:

| | |
|---|---|
| γ | 90 |
| Z | 4 |
| Z' | 2 | c) DSC (Differential Scanning Calorimetry):

The melting peak of the crystalline form (Form B) is a broad water endotherm in the DSC trace at about 65° C.

Form B represents a monohydrate polymorph of the enantiomer (1S,2S) N-[2-(2,4-dichlorophenyl)cyclobutyl]-2-(trifluoromethyl)pyridine-3-carboxamide, i.e. (1S,2S) N-[2-(2,4-dichlorophenyl)cyclobutyl]-2-(trifluoromethyl)pyridine-3-carboxamide.H$_2$O.

2.4 Form C:

a) X-Ray Powder Diffraction

The X-ray powder diffraction pattern of Form C is shown in FIG. 5.

TABLE 5

2-Theta and d-spacing values measured for Form C:

| 2-Theta | d |
|---|---|
| 10.8 | 8.2 |
| 14.5 | 6.1 |
| 17.5 | 5.1 |
| 19.0 | 4.7 |
| 23.5 | 3.8 |
| 24.5 | 3.6 |
| 26.0 | 3.4 |
| 30.2 | 3.0 |
| 32.6 | 2.7 |
| 33.3 | 2.7 |
| 34.1 | 2.6 |
| 35.5 | 2.5 | b) Single Crystal Unit Cell Parameters

TABLE 6

Crystallographic data for Form C:

| | |
|---|---|
| Unit cell volume (Å$^3$) | 877.3 |
| Calculated density (g/cm$^3$) | — |
| Space Group | P-1 |
| a (Å) | 7.27 |
| b (Å) | 9.32 |
| c (Å) | 14.11 |
| α | 75.53 |
| β | 87.03 |
| γ | 71.48 |
| Z | 2 |
| Z' | 1 | c) DSC (Differential Scanning Calorimetry):

The melting peak of the crystalline form (Form C) is a broad water endotherm in the DSC trace at about 85° C.

Form C represents a monohydrate polymorph of cis-N-[2-(2,4-dichlorophenyl)cyclobutyl]-2-(trifluoromethyl)pyridine-3-carboxamide. Form C has an enantiomer ratio (1S,2S)—N-[2-(2,4-dichlorophenyl)cyclobutyl]-2-(trifluoromethyl)pyridine-3-carboxamide to (1R,2R)—N-[2-(2,4-dichlorophenyl)cyclobutyl]-2-(trifluoromethyl)pyridine-3-carboxamide of 1 to 1, i.e. (1S,2S)—N-[2-(2,4-dichlorophenyl)cyclobutyl]-2-(trifluoromethyl)pyridine-3-carboxamide.(1R,2R)—N-[2-(2,4-dichlorophenyl)cyclobutyl]-2-(trifluoromethyl)pyridine-3-carboxamide.H$_2$O.

2.5 Form D:

a) X-Ray Powder Diffraction

Figure 10:
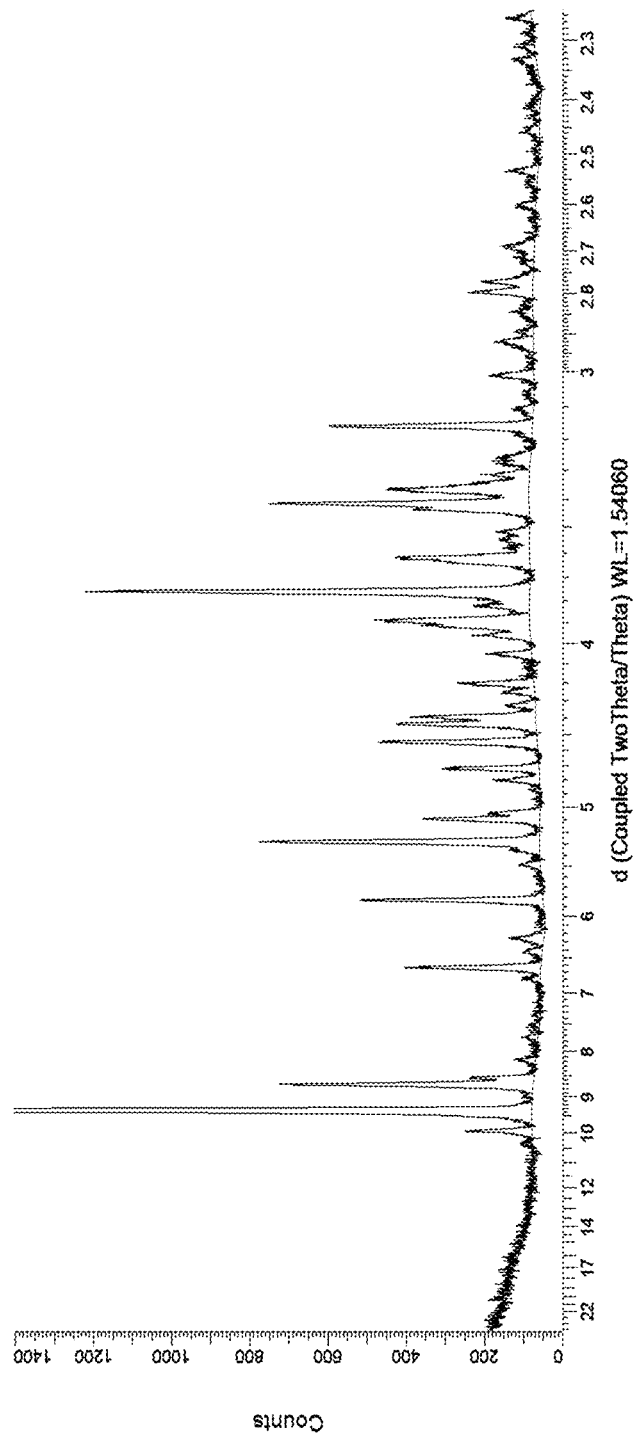
Figure 11:
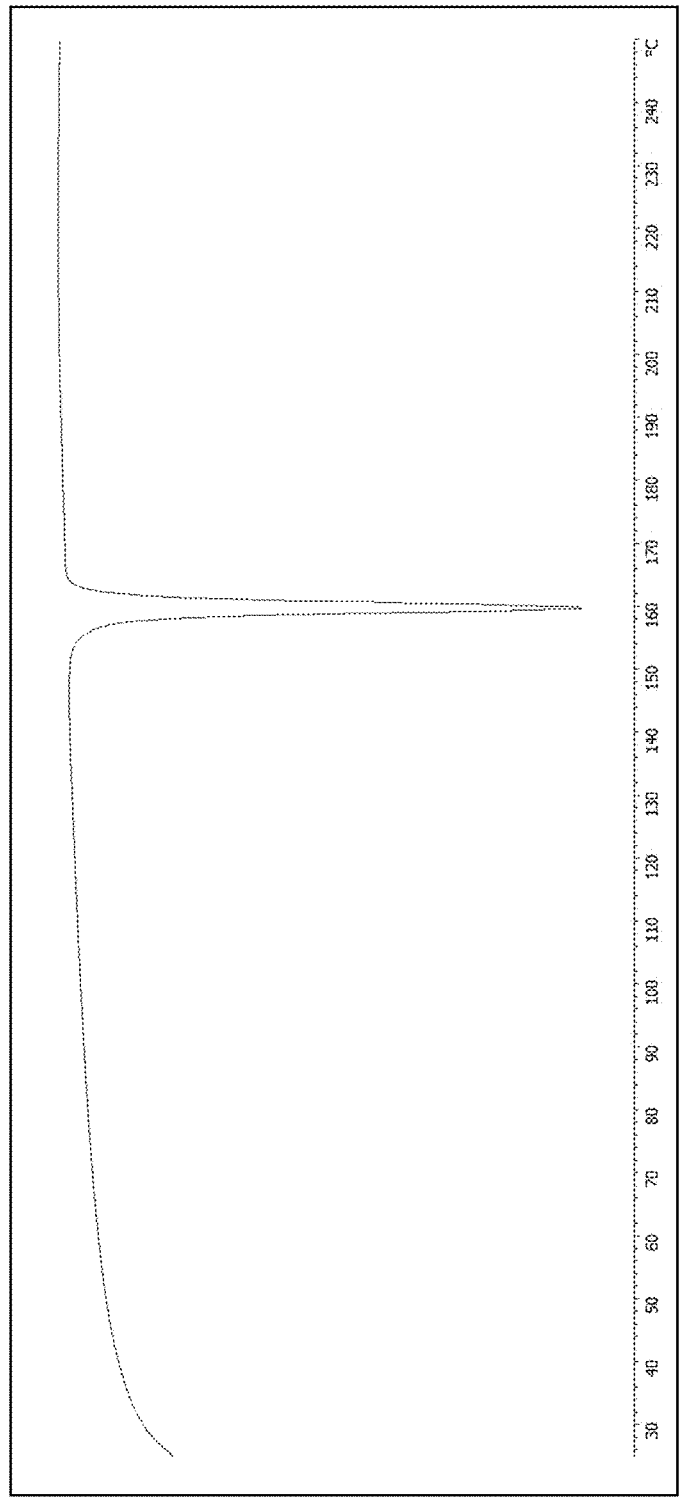

The X-ray powder diffraction pattern of Form D is shown in FIG. 10.

TABLE 7

2-Theta and d-spacing values measured for Form D:

| 2-Theta | d |
|---|---|
| 9.5 | 9.3 |
| 10.2 | 8.7 |
| 13.3 | 6.6 |
| 15.2 | 5.8 |
| 16.8 | 5.3 |
| 19.5 | 4.5 |
| 20.0 | 4.4 |
| 22.8 | 3.9 |
| 23.7 | 3.8 |
| 26.1 | 3.4 |
| 26.5 | 3.4 |
| 28.2 | 3.2 | b) DSC (Differential Scanning Calorimetry):

The melting peak of the crystalline form (Form D) in the DSC trace is at about 157° C.

3. Preparation of Formulations Comprising Form A and B

The formulations comprising polymorph Form A and B have been formulated as a flowable concentrate for seed treatment FS200 using the same recipe. The recipe used is given in Table 8:

TABLE 8

Composition of the FS200 formulations

| Role | Formulation Form A (mg) | Formulation Form B (mg) |
|---|---|---|
| Form A | 20 | — |
| Form B | — | 20 |
| Antifreeze | 1.87 | 1.87 |
| Antifoam | 0.2 | 0.2 |
| Dispersant | 8 | 8 |
| Dispersant | 2 | 2 |
| Pigment | 16.67 | 16.67 |
| Filler | Up to 100 | Up to 100 |
| Total | 100 mg | 100 mg |

The above formulations were tested for stability in a temperature cycling test as shown in FIG. 12. The formulations were then analyzed under the microscope (40×) to check for possible stability issues, in particular crystal growth and pictures were taken. FIGS. 13b and 13c show crystal growth whereas FIGS. 13a, 14a, 14b and 14c do not show any crystal growth.

The invention claimed is:

1. A crystalline form of N-[(1S,2S)-2-(2,4-dichlorophenyl)cyclobutyl]-2-(trifluoromethyl)pyridine-3-carboxamide of formula (I)

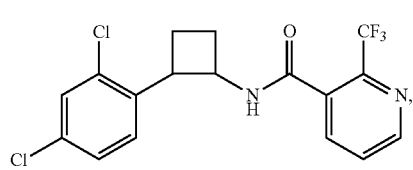

(I)

characterized by an X-ray powder diffraction pattern comprising four or more 2-theta angle values selected from the group of 6.1±0.2, 11.2±0.2, 14.0±0.2, 16.7±0.2, 17.2±0.2, 18.5±0.2, 20.8±0.2, 21.3±0.2, 22.3±0.2, 23.6±0.2, 23.9±0.2 and 24.5±0.2 at a temperature of 21-26° C.

2. The crystalline form according to claim 1, characterized by an X-ray powder diffraction pattern comprising six or more 2-theta angle values selected from the group of 6.1±0.2, 11.2±0.2, 14.0±0.2, 16.7±0.2, 17.2±0.2, 18.5±0.2, 20.8±0.2, 21.3±0.2, 22.3±0.2, 23.6±0.2, 23.9±0.2 and 24.5±0.2 at a temperature of 21-26° C.

3. The crystalline form according to claim 1, characterized by the following unit cell parameters:
a=15.52 Å±0.01 Å, b=7.24 Å±0.01 Å, c=16.64 Å±0.01 Å, α=90°±0.01°, ß=105.03°±0.01°, γ=90°±0.01°, Z=4.

4. The crystalline form according to claim 1, wherein the melting peak is at about 65° C.

5. A crystalline form of cis-N-[2-(2,4-dichlorophenyl)cyclobutyl]-2-(trifluoromethyl)pyridine-3-carboxamide of formula (I)

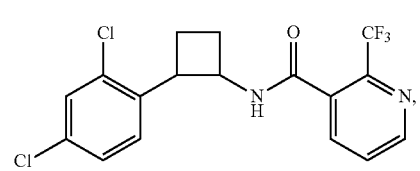

(I)

characterized by an X-ray powder diffraction pattern comprising four or more 2-theta angle values selected from the group of 10.8±0.2, 14.5±0.2, 17.5±0.2, 19.0±0.2, 23.5±0.2, 24.5±0.2, 26.0±0.2, 30.2±0.2, 32.6±0.2, 33.3±0.2, 34.1±0.2 and 35.5±0.2 at a temperature of 21-26° C.

6. The crystalline form according to claim 5, characterized by an X-ray powder diffraction pattern comprising six or more 2-theta angle values selected from the group of 10.8±0.2, 14.5±0.2, 17.5±0.2, 19.0±0.2, 23.5±0.2, 24.5±0.2, 26.0±0.2, 30.2±0.2, 32.6±0.2, 33.3±0.2, 34.1±0.2 and 35.5±0.2 at a temperature of 21-26° C.

7. The crystalline form according to claim 5, wherein the melting peak is at about 85° C.

8. The crystalline form according to claim 5, characterized by the following unit cell parameters:
a=7.27 Å±0.01 Å, b=9.32 Å±0.01 Å, c=14.11 Å±0.01 Å, α=75.53°±0.01°, ß=87.03°±0.01°, γ=71.48°±0.01°, Z=2.

9. An agricultural or pharmaceutical composition comprising the crystalline form according to claim 1 and at least one acceptable carrier or diluent.

10. The composition according to claim 9, further comprising one or more insecticidally, acaricidally, nematicidally or fungicidally active agents.

11. A method of protecting crops of useful plants against damages caused by nematode pests, which comprises treating the plants or the locus thereof with a composition according to claim 9.

12. A method of protecting a plant propagation material against damages caused by nematode pests, which comprises treating the material with a composition according to claim 9.

13. A method of protecting crops of useful plants against damages caused by fungi, which comprises treating the plants or the locus thereof with a composition according to claim 9.

14. A method of protecting plant propagation material against damages caused by fungi, which comprises treating this material with a composition according to claim 9.

* * * * *